United States Patent
Assaraf et al.

(10) Patent No.: US 11,530,447 B2
(45) Date of Patent: Dec. 20, 2022

(54) METHODS AND KITS FOR EVALUATING ZINC LEVELS IN MILK

(71) Applicant: TECHNION RESEARCH & DEVELOPMENT FOUNDATION LTD., Haifa (IL)

(72) Inventors: Yehuda G. Assaraf, Rakefet (IL); Yarden Golan Maor, Moshav Merchavia (IL)

(73) Assignee: TECHNION RESEARCH & DEVELOPMENT FOUNDATION LIMITED, Haifa (IL)

(*) Notice: Subject to any disclaimer, the term of this patent is extended or adjusted under 35 U.S.C. 154(b) by 416 days.

(21) Appl. No.: 16/603,613

(22) PCT Filed: Apr. 11, 2018

(86) PCT No.: PCT/IL2018/050416
§ 371 (c)(1),
(2) Date: Oct. 8, 2019

(87) PCT Pub. No.: WO2018/189743
PCT Pub. Date: Oct. 18, 2018

(65) Prior Publication Data
US 2020/0040396 A1 Feb. 6, 2020

Related U.S. Application Data

(60) Provisional application No. 62/484,365, filed on Apr. 11, 2017.

(51) Int. Cl.
| | |
|---|---|
| *C12Q 1/68* | (2018.01) |
| *C12P 19/34* | (2006.01) |
| *C12Q 1/6883* | (2018.01) |
| *G01N 33/487* | (2006.01) |

(52) U.S. Cl.
CPC ......... *C12Q 1/6883* (2013.01); *G01N 33/487* (2013.01); *C12Q 2600/156* (2013.01)

(58) Field of Classification Search
CPC .................. C12Q 1/6883; C12Q 2600/156
See application file for complete search history.

(56) References Cited

U.S. PATENT DOCUMENTS

2005/0106675 A1 5/2005 Wei et al.

OTHER PUBLICATIONS

GenBank Locus NM_001004434 "*Homo sapiens* solute carrier family 30 member 2 (SLC30A2), transcript variant 1, mRNA", Mar. 7, 2016. 4 pages printed from https://www.ncbi.nlm.nih.gov/ (Year: 2016).*
"Zinc transporter SLC30A2 genetic variations and health implications" A Thesis submitted to the Faculty of Graduate Studies of The University of Manitoba by Sandra Castillo San Juan. (Year: 2014).*
Naoya Itsumura et al., "Novel mutations in SLC30A2 involved in the pathogenesis of transient neonatal zinc deficiency", Pediatric Research, vol. 80 pp. 586-594, May 16, 2016. Retrieved Aug. 23, 2021; doi: 10.1038/or.2016.108.
Yarden Golan, et al., "Molecular basis of transient neonatal zinc deficiency novel ZnT2 mutations disrupting zinc binding and permeation", Journal of Biological Chemistry, vol. 291 Issue 26 pp. 13546-13559, Jun. 24, 2016. Retrieved Aug. 23, 2021 from: http://www.jbc.org/cgi/doi/10.1074/jbc.M116.732693.
Naoya Itsumura et al., "Compound heterozygous mutations in SLC30A2/ZnT2 results in low milk zinc concentralions: a novel mechanism for zinc deficiency in a breast-fed infant", Plos one, vol. 8 Issue 5, pp. e64045, May 2013. Retrieved Aug. 23, 2021; doi: 10.1371/journal.pone.0064045.
Miguel Lova Navarro et al., "Transient neonatal zinc deficiency due to a new autosomal dominant mutation in gene SLC30A2 (ZnT-2)." Pediatric dermatology, vol. 31 Issue 2 pp. 251-252, Mar.-Apr. 2014. Retrieved Aug. 23, 2021; doi: 10.1111/pde.12257.
Danielle G. Lemay et al., "Sequencing the transcriptome of milk production: milk trumps mammary tissue." BMC genomics, vol. 14 Issue 1 p. 872, Dec. 12, 2013. Retrieved Aug. 23, 2021 from: http://www.biomedcentral.com/1471-2164/14/872.
Winyoo Chowanadisai et al., "Identification of a mutation in SLC30A2 (ZnT-2) in women with low milk zinc concentralion that results in transient neonatal zinc deficiency", Journal of Biological Chemistry, vol. 281 Issue 51 pp. 39699-39707, Oct. 25, 2006. Retrieved Aug. 23, 2021; DOI: 10.1074/jbc.M605821200.
Inbal Lasry et al., "A dominant negative heterozygous G87R mutation in the zinc transporter, ZnT-2 (SLC30A2) Yesults in transient neonatal zinc deficiency", Journal of Biological Chemistry, vol. 287 Issue 35 pp. 29348-29361, Aug. 24, 2012. Retrieved Aug. 23, 2021; DOI: 10.1074/jbc.M112.368159.
Yarden Golan, et al., "Identification of Genetic Diseases Using Breast Milk Cell Analysis: The Case of Transient Neonatal Zinc Deficiency (TNZD)", Cellular & Molecular Medicine, vol. 3 Issue 2, May 23, 2017. Retrieved Aug. 23, 2021; DOI: 10.21767/2573-5365.100031.
"*Homo sapiens* solute carrier family 30 member 2 (SLC30A2), transcript variant 1, mRNA", GeneBank accession No. NM_001004434. 2, URL: <https://www.ncbi.nlm.nih.gov/nucleotide/NM_001004434. 2?report=genbank&log$=nucltop&blast_rank=1&RID=MUZGEFTM015, Apr. 15, 1996 (Apr. 15, 1996).
Antonia Kienast et al., "Zinc-deficiency dermatitis in breast-fed infants", European Journal of Pediatrics, vol. 166 Issue 3 pp. 189-194. 2007. Retrieved Aug. 23, 2021; 10.1007/S00431-006-0218-9.
Maria Consolata Miletta et al., "Transient Neonatal Zinc Deficiency Caused by a Heterozygous G87R Mutation in the Zinc Transporter ZnT-2 (SLC30A2) Gene in the Mother Highlighting the Importance of Zn2+ for Normal Growth and Development", International Journal of Endocrinology, vol. 2013 Issue 7386, 2013 Retrieved Aug. 23, 2021 from http://dx.doi.org/10.1155/2013/259189.

(Continued)

*Primary Examiner* — Stephen T Kapushoc
(74) *Attorney, Agent, or Firm* — The Roy Gross Law Firm, LLC; Roy Gross

(57) ABSTRACT

The present invention is directed to methods and kits for determining the presence of a mutated SLC30A2 polynucleotide. The invention is further directed to methods of determining a subject's genetic-susceptibility to zinc deficiency and evaluating zinc levels in a composition comprising breast milk.

12 Claims, 10 Drawing Sheets
(2 of 10 Drawing Sheet(s) Filed in Color)
Specification includes a Sequence Listing.

(56) References Cited

OTHER PUBLICATIONS

Linxi Qian, et al., "Polymorphisms of SLC30A2 and selected perinatal factors associated with low milk zinc in Chinese breastfeeding women", Early Human Development, vol. 88 Issue 8 pp. 663-668, 2012. Retrieved Aug. 23, 2021; doi:10.1016/j.earlhumdev.2012.01.011.

Josiane Arnaud, et al., "Determination of ultrafiltrable zinc in human milk by electrothermal atomic absorption spectrometry", The Analyst, vol. 117 Issue 10 p. 1593,1992.

Rokunohe D, Nakano H, Sawamura D. Transient neonatal zinc deficiency. Japanese J. Clin. Dermatology 2015; 69; 27-30.

Yarden Golan et al., "Heterodimerization, Altered Subcellular Localization, and Function of Multiple Zinc Transporters in Viable Cells Using Bimolecular Fluorescence Complementation", Journal of Biological Chemistry, vol. 290 Issue 14 pp. 9050-9063, 2015. Retrieved Aug. 23, 2021; DOI 10.1074/jbc.M114.617332.

Jose G. Dorea, "Zinc in human milk", Nutritional Research, vol. 20 Issue 11 pp. 1645-1687, 2000. Retrieved Aug. 23, 2021 from: https://www.scribd.com/document/396042799/Zinc-in-Human-Milk.

Yarden Golan et al., "The role of the zinc transporter SLC30A2/ZnT2 in transient neonatal zinc deficiency", Mietallomics, Issue 9 pp. 1352-1366, 2017. Retrieved Aug. 23, 2021; DOI: 10.1039/c7mt00162b.

Taiho Kambe et al. The Physiological, Biochemical, and Molecular Roles of Zinc Transporters in Zinc Homeostasis and Metabolism. Physiol Rev., vol. 95 Issue 3 pp. 749-784, 2015. Retrieved Aug. 23, 2021; doi:10.1152/physrev.00035.2014.

Tomoki Kimura and Taiho Kambe, "The functions of metallothionein and ZIP and ZnT transporters: An overview and perspective", Int. J Mol. Sci., vol. 17 Issue 3 p. 336, 2016. Retrieved Aug. 23, 2021; doi: 10.3390/ijms17030336.

Yonatan Perez et al., "SLC30A9 mutation affecting intracellular zinc homeostasis causes a novel cerebro-renal syndrome", Brain, vol. 140 Issue 4 pp. 928-939, 2017. Retrieved Aug. 23, 2021; doi:10.1093/brain/awx013.

David J Eide, "Zinc transporters and the cellular trafficking of zinc", Biochim Biophys Acta—Mol Cell Res, vol. 1763 Issue 7 pp. 711-722, 2006. Retrieved Aug. 23, 2021; doi:10.1016/j.bbamcr.2006.03.005.

Helmut Grasberger and Samuel Refetoff, "Genetic causes of congenital hypothyroidism due to dyshormonogenesis", Curr. Opin. Pediatr. vol. 23 Issue 4 pp. 421-428, 2011. Retrieved Aug. 23, 2021; DOI:10.1097/MOP.0b013e32834726a4.

Maynika V Rastogi and Stephen H LaFranchi, "Congenital hypothyroidism", Orphanet J Rare Dis, vol. 10 Issue 5 p. 17, 2010. Retrieved Aug. 23, 2021 from: http://www.ojrd.eom/content/5/1/17.

Guy Van Vliet and Johnny Deladoëy, "Diagnosis, Treatment and Outcome of Congenital Hypothyroidism", Endocr Dev, vol. 26 Issue 50 p. 9, 2014 Retrieved Aug. 23, 2021; DOI: 10.1159/000363155.

Stephanie M Carleton et al., "DNA Carrier Testing and Newborn Screening for Maple Syrup Urine Disease in Old Order Mennonite Communities", Genet Test Mol Biomarkers, vol. 14 Issue 2 pp. 205-208, 2010. Retrieved Aug. 23, 2021; DOI: 10.1089=gtmb.2009.0107.

Pamela Harris-Haman et al., "Implications of Maple Syrup Urine Disease in Newborns", Nurs Womens Health vol. 21 Issue 3 pp. 196-206, 2017. Retrieved Aug. 23, 2021 from: http://dx.doi.org/10.1016/j.nwh.2017.04.009.

Wei Li Yang et al., "Transient zinc deficiency syndrome in a breast-fed infant due to decreased zinc in breast milk (type II hypozincemia of infancy): A case report and review of the literature", vol. 30 Issue 2 pp. 66-70, 2012. Retrieved Aug. 23, 2021; doi: 10.1016/j dsi.2011.09.013.

Takafumi Obara et al., "Zinc deficiency in low zinc breast milk by maternal ZnT2 gene mutation" The Journal of the Japan Pediatric Society, vol. 120 Issue 11, Nov. 2016.

Hui M Liew et al., "Transient Neonatal Zinc Deficiency Caused by a Novel Mutation in the SLC30A2 Gene", Pediatr Dermatol, vol. 34 Issue 2 pp. e104-e105, 2017. Retrieved Aug. 23, 2021; DOI: 10.1111/pde.13065.

Ananda S Prasad et al., "Syndrome of iron deficiency anemia, hepatosplenomegaly, hypogonadism, dwarfism and geophagia". Am J Med vol. 31 pp. 532-546, 1961.

Sunil Sazawal et al. "Zinc Supplementation does not Affect the Breast Milk Zinc Concentration of Lactating Women Belonging to Low Socioeconomic Population", Journal of Human Nutrition and Food Science vol. 1 Issue 2 p. 1014, 2013. Retrieved Aug. 23, 2021 from: https://www.jscimedcentral.com/Nutrition/Articles/nutrition-1-1014.pdf.

Nenad Blau, "Genetics of Phenylketonuria: Then and Now", Hum Mutat vol. 37 Issue 6 pp. 508-515, 2016. Retrieved Aug. 23, 2021; DOI: 10.1002/humu.22980.

Monkol Lek et al., "Analysis of protein-coding genetic variation in 60,706 humans", Nature vol. 536 Issue 7616 pp. 285-291, 2016 Retrieved Aug. 23, 2021; doi:10.1038/nature19057.

Haim Ashkenazy et al., "ConSurf 2010: calculating evolutionary conservation in sequence and structure of proteins and nucleic acids", Nucleic Acids Res. vol. 38 Web Server Issue pp. W529-33, 2010. Retrieved Aug. 23, 2021 doi:1 0.1093/nar/gkq399.

Haim Ashkenazy et al., "ConSurf 2016: an improved methodology to estimate and visualize evolutionary conservation in macromolecules", Nucleic Acids Res. vol. 44 Web Server Issue pp. W344-50, 2016. Retrieved Aug. 23, 2021 Joi: 10.1093/nar/gkw408.

Meytal Landau et al., "ConSurf 2005: the projection of evolutionary conservation scores of residues on protein structures", Nucleic Acids Res. vol. 33 Web Server Issue pp. W299-W302, 2005. Retrieved Aug. 23, 2021; doi:10.1093/nar/gki370.

Fabian Glaser et al., "ConSurf: identification of functional regions in proteins by surface-mapping of phylogenetic information", Bioinformatics vol. 19 Issue 1 pp. 163-164, 2003.

Yongwook Choi et al., "Predicting the Functional Effect of Amino Acid Substitutions and Indels", PLoS One vol. 7 Issue 10 p. e46688, 2012. Retrieved Aug. 23, 2021 from: http://doi.acm.org/10.1145/2382936.2382989.

Yongwook Choi, "Fast Computation of Pairwise Sequence Alignment Scores Between a Protein and a Set of Single-Locus Variants of Another Protein", BCB '12: Proceedings of the ACM Conference on Bioinformatics, Computational Biology and Biomedicine, pp. 414-417, Oct. 2012.

Ivan A Adzhubei et al., "A method and server for predicting damaging missense mutations", Nat Methods vol. 7 Issue 4 pp. 248-249, 2010.

Aron Broom et al., "Computational tools help improve protein stability but with a solubility tradeoff", J Biol Chem, vol. 292 Issue 35 pp. 14349-61, 2017. Retrieved Aug. 23, 2021; doi: 10.1074/jbc.M117.784165.

Inbal Lasry et al., "In situ dimerization of multiple wild type and mutant zinc transporters in live cells using bimolecular fluorescence complementation", Journal of Biological Chemistry, vol. 289 Issue 11 pp. 7275-7292, 2014. Retrieved Aug. 23, 2021; DOI 10.1074/jbc.M113.533786.

Konrad J. Karczewski et al.: "The ExAC browser: displaying reference data information from over 60 000 exomes", D840-D845, Nucleic Acids Research, 2017, vol. 45, Database issue. Retrieved Aug. 23, 2021; doi: 10.1093/nar/gkw971.

Jose G.Dorea: "Zinc in human milk", Nutrition Research, vol. 20, Issue 11, Nov. 2000, pp. 1645-1687.

PCT International Search Report for International Application No. PCT/IL2018/050416, dated Aug. 5, 2018, 4pp.

PCT Written Opinion for International Application No. PCT/IL2018/050416, dated Aug. 5, 2018, 7pp.

PCT International Preliminary Report on Patentability for International Application No. PCT/IL2018/050416, dated Oct. 15, 2019, 8pp.

* cited by examiner

SEQ ID NO: 17

■ benign  ■ somewhat conserved  ■ conserved  ● very conserved

■ damaging  ■ benign

* probably damaging   * possibly damaging   * benign

SEQUENCE LISTING

```
<160> NUMBER OF SEQ ID NOS: 18

<210> SEQ ID NO 1
<211> LENGTH: 1118
<212> TYPE: DNA
<213> ORGANISM: Homo sapiens

<400> SEQUENCE: 1
atggaggcca aggagaagca gcatctgttg gacgccaggc cggcaatccg gtcatacacg      60
ggatctctgt ggcaggaagg ggctggctgg attcctctgc cccgacctgg cctggacttg     120
caggccattg agctggctgc ccagagcaac catcactgcc atgctcagaa gggtcctgac     180
agtcactgtg accccaagaa ggggaaggcc cagcgccagc tgtatgtagc ctctgccatc     240
tgcctgttgt tcatgatcgg agaagtcgtt ggtgggtacc tggcacacag cttggctgtc     300
atgactgacg cagcacacct gctcactgac tttgccagca tgctcatcag cctcttctcc     360
ctctggatgt cctcccggcc agccaccaag accatgaact ttggctggca gagagctgag     420
atcttgggag ccctggtctc tgtactgtcc atctgggtcg tgacgggggt actggtgtac     480
ctggctgtgg agcggctgat ctctggggac tatgaaattg acgggggggac catgctgatc     540 acgtcgggct gcgctgtggc tgtgaacatc ataatggggt tgacccttca ccagtctggc     600
catgggcaca gccacggcac caccaaccag caggaggaga accccagcgt ccgagctgcc     660
ttcatccatg tgatcggcga ctttatgcag agcatgggtg tcctagtggc agcctatatt     720
ttatacttca agccagaata caagtatgta gaccccatct gcaccttcgt cttctccatc     780
```

```
ctggtcctgg ggacaacctt gaccatcctg agagatgtga tcctggtgtt gatggaaggg      840
acccccaagg gcgttgactt cacagctgtt cgtgatctgc tgctgtcggt ggaggggta       900 gaagccctgc acagcctgca tatctgggca ctgacggtgg cccagcctgt tctgtctgtc      960
cacatcgcca ttgctcagaa tacagacgcc caggctgtgc tgaagacagc cagcagccgc     1020
ctccaaggga agttccactt ccacaccgtg accatccaga tcgaggacta ctcggaggac     1080
atgaaggact gtcaggcatg ccagggcccc tcagactg                            1118
```

```
<210> SEQ ID NO 2
<211> LENGTH: 20
<212> TYPE: DNA
<213> ORGANISM: Artificial
<220> FEATURE:
<223> OTHER INFORMATION: Synthetic

<400> SEQUENCE: 2
actgcatgga ggccaaggag                                                   20

<210> SEQ ID NO 3
<211> LENGTH: 19
<212> TYPE: DNA
<213> ORGANISM: Artificial
<220> FEATURE:
<223> OTHER INFORMATION: Synthetic

<400> SEQUENCE: 3
gtcgccgatc acatggatg                                                    19

<210> SEQ ID NO 4
<211> LENGTH: 21
<212> TYPE: DNA
<213> ORGANISM: Artificial
<220> FEATURE:
<223> OTHER INFORMATION: Synthetic

<400> SEQUENCE: 4
ctggtgtacc tggctgtgga g                                                 21

<210> SEQ ID NO 5
<211> LENGTH: 21
<212> TYPE: DNA
<213> ORGANISM: Artificial
<220> FEATURE:
<223> OTHER INFORMATION: Synthetic

<400> SEQUENCE: 5
tgagcagtca gtctgagggg c                                                 21

<210> SEQ ID NO 6
<211> LENGTH: 22
<212> TYPE: DNA
<213> ORGANISM: Artificial
<220> FEATURE:
<223> OTHER INFORMATION: Synthetic

<400> SEQUENCE: 6
gatcctggtg ttgatggatg ct                                                22

<210> SEQ ID NO 7
<211> LENGTH: 21
<212> TYPE: DNA
<213> ORGANISM: Artificial
<220> FEATURE:
<223> OTHER INFORMATION: Synthetic
```

```
<400> SEQUENCE: 7
tgagcagtca gtctgagggg c                                              21

<210> SEQ ID NO 8
<211> LENGTH: 20
<212> TYPE: DNA
<213> ORGANISM: Artificial
<220> FEATURE:
<223> OTHER INFORMATION: Synthetic

<400> SEQUENCE: 8
ccaagggcgt tgacttcaca                                                20

<210> SEQ ID NO 9
<211> LENGTH: 25
<212> TYPE: DNA
<213> ORGANISM: Artificial
<220> FEATURE:
<223> OTHER INFORMATION: Synthetic

<400> SEQUENCE: 9
gatgtggaca gacagaacag gctgg                                          25

<210> SEQ ID NO 10
<211> LENGTH: 30
<212> TYPE: DNA
<213> ORGANISM: Artificial Sequence
<220> FEATURE:
<223> OTHER INFORMATION: Synthetic

<400> SEQUENCE: 10
atactcgaga ccatgaacag cctgatcaaa                                     30

<210> SEQ ID NO 11
<211> LENGTH: 30
<212> TYPE: DNA
<213> ORGANISM: Artificial Sequence
<220> FEATURE:
<223> OTHER INFORMATION: Synthetic

<400> SEQUENCE: 11
atactcgaga ccatgaacag cctgatcaaa                                     30

<210> SEQ ID NO 12
<211> LENGTH: 1960
<212> TYPE: DNA
<213> ORGANISM: Homo sapiens

<400> SEQUENCE: 12
ggccgcgggg cgcagcggct gacccgagac acgggagcgc ttggcacgcg gagccagagc    60
cggagctgca gccgcagcgg gagccggggg agctcagggg ccgcaggagc cgggccggag   120
tgagcgcacc tcgcggggcc ctcggggcag gtggtgagc gccacccgga gtcccgcgcg    180
caactttcag ggcgcactcg gcggggcggc tgcgcggctg ccgggactcg gcgcgggact   240
gcatggaggc caaggagaag cagcatctgt tggacgccag gccggcaatc cggtcataca   300
cgggatctct gtggcaggaa ggggctggct ggattcctct gccccgacct ggcctggact   360
tgcaggccat tgagctggct gcccagagca accatcactg ccatgctcag aagggtcctg   420
acagtcactg tgaccccaag aaggggaagg cccagcgcca gctgtatgta gcctctgcca   480
tctgcctgtt gttcatgatc ggagaagtcg ttggtgggta cctggcacac agcttggctg   540
```

```
tcatgactga cgcagcacac ctgctcactg actttgccag catgctcatc agcctcttct    600
ccctctggat gtcctcccgg ccagccacca agaccatgaa ctttggctgg cagagagctg    660
agatcttggg agccctggtc tctgtactgt ccatctgggt cgtgacgggg gtactggtgt    720
acctggctgt ggagcggctg atctctgggg actatgaaat tgacggggggg accatgctga    780
tcacgtcggg ctgcgctgtg gctgtgaaca tcataatggg gttgacccttt caccagtctg    840
gccatgggca cagccacggc accaccaacc agcaggagga gaaccccagc gtccgagctg    900
ccttcatcca tgtgatcggc gactttatgc agagcatggg tgtcctagtg gcagcctata    960
tttttatactt caagccagaa tacaagtatg tagaccccat ctgcaccttc gtcttctcca   1020
tcctggtcct ggggacaacc ttgaccatcc tgagagatgt gatcctggtg ttgatggaag   1080
ggaccccccaa gggcgttgac ttcacagctg ttcgtgatct gctgctgtcg gtggagggggg   1140
tagaagccct gcacagcctg catatctggg cactgacggt ggcccagcct gttctgtctg   1200
tccacatcgc cattgctcag aatacagacg cccaggctgt gctgaagaca gccagcagcc   1260
gcctccaagg gaagttccac ttccacaccg tgaccatcca gatcgaggac tactcggagg   1320
acatgaagga ctgtcaggca tgccagggcc cctcagactg actgctcagc caggcaccaa   1380
ctgggggcatg aacaggacct gcaggtggct ggactgagtg tcccccaggc ccagccagga   1440
cttttgcctac cccagctgtg ttgtaaacca ggtccccctc ctgacctctg ccccactcca   1500
ggaatggagc tcttcccagc ctcccatctg actacagcca gggtggggac tcagcgggta   1560
taaagctagt gtgaccctgc tcttccagct cctgggccag ctctggaagg gctgtatttg   1620
ggcctaatcc tcagcaaatg ttctaccact cgcaggggca aaggtggtga gccacgggac   1680
gtccaagggg aggctggccc cagcgcgccc atactgcctg cctcatgccc cattctcagc   1740
ctggctggcc tttgcccttta tgaatctgag cccctccatc tgcctatagc aataggcacg   1800
ggggtgagga ccctcacact ctcatttgag cctccctgag gcagggagcc aggaggcacc   1860
tgaggcctat ctgtgcctta gtcacttcag ctatgagcca aatgttccct ttcctggagg   1920
ggagaggctt cttactaggt aagagacagg tttcctcttt                           1960
```

<210> SEQ ID NO 13
<211> LENGTH: 23
<212> TYPE: PRT
<213> ORGANISM: Homo sapiens

<400> SEQUENCE: 13

Val Ile Leu Val Leu Met Glu Gly Thr Pro Lys Gly Val Asp Phe Thr
1               5                   10                  15

Ala Val Arg Asp Leu Leu Leu
            20

<210> SEQ ID NO 14
<211> LENGTH: 14
<212> TYPE: PRT
<213> ORGANISM: Homo sapiens

<400> SEQUENCE: 14

Val Ile Leu Val Leu Met Glu Ala Val Arg Asp Leu Leu Leu
1               5                   10

<210> SEQ ID NO 15
<211> LENGTH: 29
<212> TYPE: DNA
<213> ORGANISM: Artificial Sequence
<220> FEATURE:

```
<223> OTHER INFORMATION: Synthetic

<400> SEQUENCE: 15
ggtgttgatg aagctgttc gtgatctgc                                    29

<210> SEQ ID NO 16
<211> LENGTH: 29
<212> TYPE: DNA
<213> ORGANISM: Artificial Sequence
<220> FEATURE:
<223> OTHER INFORMATION: Synthetic

<400> SEQUENCE: 16
gcagatcacg aacagcttcc atcaacacc                                   29

<210> SEQ ID NO 17
<211> LENGTH: 15
<212> TYPE: DNA
<213> ORGANISM: Homo sapiens

<400> SEQUENCE: 17
tcctcagkga ccccc                                                  15

<210> SEQ ID NO 18
<211> LENGTH: 15
<212> TYPE: DNA
<213> ORGANISM: Homo sapiens

<400> SEQUENCE: 18
ggaagggacc cccaa                                                  15
```

METHODS AND KITS FOR EVALUATING ZINC LEVELS IN MILK

CROSS REFERENCE

This application is a National Phase of PCT Patent Application No. PCT/IL2018/050416 having International filing date of Apr. 11, 2018, which claims the benefit of priority of U.S. Provisional Patent Application No. 62/484,365 filed Apr. 11, 2017. The contents of the above referenced applications are incorporated herein by reference in their entirety.

FIELD OF INVENTION

The present invention is in the field of diagnosis, and particularly directed to detecting a mineral deficiency in breast milk.

BACKGROUND OF THE INVENTION

Zinc is vital for the structure and function of ~10% of the human proteome. Since zinc is bound to myriad proteins and sequestered in organelles, the cytoplasmic zinc concentration is very low being at the pM-nM range. Zinc homeostasis is tightly regulated by two families of proteins known as Zips and ZnTs. Zips import zinc into the cytoplasm from the lumen of organelles or through the plasma membrane from the extracellular milieu. In contrast, ZnTs compartmentalize zinc within organelles or export zinc to the extracellular milieu. In addition, there are also non-specific metal chelators termed metallothioneins (MTs) which efficiently bind excess zinc. Tight regulation of the intracellular zinc level is crucial for cell survival and hence human health. Impaired zinc homeostasis has an adverse effect on the physiology of the organism, and loss of function (LoF) mutations in zinc transporters lead to various diseases.

Cumulative evidence indicates that some exclusively breastfed infants suffer from severe zinc deficiency due to lack of zinc in the breast milk they consume. The main initial symptoms of zinc deficiency are dermatitis, diarrhea, alopecia, and loss of appetite. However, some cases of zinc deficiency are misdiagnosed, and infants are treated with drugs against eczema or impetigo. Infants are particularly vulnerable to zinc deficiency as they require large amounts of zinc for their normal growth and development. In this respect, preterm infants are born with low hepatic zinc stores and display a low intestinal zinc absorption capacity; hence, they are more prone to zinc deficiency in the first months of life.

Transient neonatal zinc deficiency (TNZD; OMIM #608118) appears in exclusively breastfed infants as a result of low zinc concentration in the breast milk of their nursing mothers. Thus, infants harboring TNZD have no zinc absorption impairment and are completely cured after zinc supplementation of their breast milk and after weaning. TNZD is predominantly a result of loss of function mutations in the SLC30A2 gene (Chowanadisai W., et al., Journal of Biological Chemistry, 2006, 281(51):39699-39707; Golan Y, et al., Journal of Biological Chemistry, 2016, 291(26):13546-13559; Itsumura N., et al., PLoS One, 2013, 8(5):e64045; Itsumura N, et al., Pediatric Research, 2016, 80(4):586-94; Lova Navarro M., et al., European Journal of Pediatrics, 2007, 166(3):189-194; Miletta M C., et al., International Journal of Endocrinology, 2013, 2013:259189; Qian L., et al., Early Human Development, 2012, 88(8): 663-668). SLC30A2 encodes for the zinc transporter ZnT2 which is responsible for zinc accumulation in intracellular vesicles, and in lactating mammary epithelial gland cells. Through exocytosis, these zinc-loaded vesicles secrete zinc into breast milk. These epithelial cells can also be found in and extracted from the milk itself, as some are sloughed off into the milk. Excluding one case of compound ZnT2 mutations (Itsumura N., et al., PLoS One, 2013), and two cases with no detectable mutations in the coding region of SLC30A2 (although the promoter region was not sequenced), all TNZD cases reported to date were found in mothers harboring heterozygous loss of function mutations in the SLC30A2 gene.

Breast milk zinc concentrations vary largely within and between mothers at different stages of lactation. As a result, it is difficult to determine the reference levels of zinc concentration in human breast milk. However, it appears that in cases of TNZD, zinc levels in breast milk are much lower compared to control breast milk determinations from the first days of lactation. Taking into consideration the large variability in zinc concentrations in breast milk, and the fact that there is no gold standard method for reliable quantification of zinc concentration in breast milk, it remains highly essential to develop a reliable, easy, rapid, and non-invasive tool for early diagnosis of TNZD.

SUMMARY OF THE INVENTION

The present invention provides methods for evaluating zinc levels in a composition comprising milk, comprising screening a SLC30A2 polynucleotide, for a mutation, as well as kits for evaluating same. There is also provided methods for reducing the risk of a zinc deficiency in a subject consuming a composition comprising milk, comprising evaluating zinc levels in the composition prior to consumption.

According to one aspect, there is provide a method for evaluating zinc levels in a breast milk, comprising: (i) providing a composition comprising breast milk, and (ii) screening for a mutation in a SLC30A2 polynucleotide, wherein detection of said mutation in said SLC30A2 polynucleotide, indicates that said breast milk has a low zinc content, thereby evaluating zinc levels in a breast milk.

According to another aspect, there is provided a method for reducing the risk of zinc deficiency in a breastfed infant, comprising: (i) providing a composition comprising breast milk, and (ii) screening for a mutation in a SLC30A2 polynucleotide, wherein detection of said mutation in said SLC30A2 polynucleotide, indicates that said composition has a low zinc content, thereby reducing the risk of zinc deficiency in the breastfed infant.

In some embodiments, the composition is consumed by an infant and the method further comprises diagnosing transient neonatal zinc deficiency (TNZD) in the infant, wherein detection of the mutation determines the infant is afflicted with TNZD.

In some embodiments, the SLC30A2 polynucleotide comprises a polynucleotide sequence as set forth in SEQ ID NO: 1. In some embodiments, the SLC30A2 polynucleotide is a DNA molecule, mRNA molecule or cDNA molecule made from said mRNA molecule.

In some embodiments, the mutation reduces stability of a mRNA, reduces translation of a mRNA, reduces the level of ZnT2 protein produced, reduces homodimerization of ZnT2 protein produced, reduces zinc binding by ZnT2 protein produced, reduces zinc transport by ZnT2 protein produced, or a combination thereof.

In some embodiments, the polynucleotide mutation is selected from the group consisting of: mutation of adenine 161, mutation of guanine 259, mutation of thymine 454, deletion of cytosine 663, mutation of guanine 838, mutation of guanine 839, deletion of bases 840-866, mutation of cytosine 887, mutation of cytosine 935, and mutation of guanine 1,063. In some embodiments, the mutation is mutation of guanine 839 or deletion of bases 840-866. In some embodiments, guanine 839 is mutated to thymine.

In some embodiments, the polynucleotide mutation comprises mutation of cytosine 839. In some embodiments, cytosine 839 is mutated to adenosine.

In some embodiments, the screening comprises sequencing of the polynucleotide. In some embodiments, the sequencing employs at least one oligonucleotide with at least 70% homology to at least one sequence selected from the group consisting of: ACTGCATGGAGGCCAAGGAG (SEQ ID NO: 2), GTCGCCGATCACATGGATG (SEQ ID NO: 3), CTGGTGTACCTGGCTGTGGAG (SEQ ID NO: 4), or TGAGCAGTCAGTCTGAGGGGC (SEQ ID NO: 5). In some embodiments, the sequencing employs at least one oligonucleotide comprising at least one sequence selected from the group consisting of:

```
ACTGCATGGAGGCCAAGGAG,     (SEQ ID NO: 2)

GTCGCCGATCACATGGATG,      (SEQ ID NO: 3)

CTGGTGTACCTGGCTGTGGAG,    (SEQ ID NO: 4)
or

TGAGCAGTCAGTCTGAGGGGC.    (SEQ ID NO: 5)
```

In some embodiments, the screening comprises PCR analysis of a DNA or a cDNA polynucleotide. In some embodiments, the PCR analysis employs at least one oligonucleotide with at least 70% homology to at least one sequence selected from the group consisting of: GATCCTGGTGTTGATGGATGCT (SEQ ID NO: 6), TGAGCAGTCAGTCTGAGGGGC (SEQ ID NO: 7), CCAAGGGCGTTGACTTCACA (SEQ ID NO: 8) and GATGTGGACAGACAGAACAGGCTGG (SEQ ID NO: 9). In some embodiments, the PCR analysis employs at least one oligonucleotide comprising at least one sequence selected from the group consisting of: GATCCTGGTGTTGATGGATGCT (SEQ ID NO: 6), TGAGCAGTCAGTCTGAGGGGC (SEQ ID NO: 7), CCAAGGGCGTTGACTTCACA (SEQ ID NO: 8) and GATGTGGACAGACAGAACAGGCTGG (SEQ ID NO: 9). In some embodiments, the PCR analysis employs at least one oligonucleotide with at least 70% homology to the sequence GATCCTGGTGTTGATGGATGCT (SEQ ID NO: 6). In some embodiments, the PCR analysis employs at least one oligonucleotide comprising the sequence GATCCTGGTGTTGATGGATGCT (SEQ ID NO: 6). In some embodiments, the PCR analysis employs at least one oligonucleotide with at least 70% homology to the sequence CCAAGGGCGTTGACTTCACA (SEQ ID NO: 8). In some embodiments, the PCR analysis employs at least one oligonucleotide comprising the sequence CCAAGGGCGTTGACTTCACA (SEQ ID NO: 8).

According to another aspect, there is provided a kit for evaluating zinc levels in a composition comprising breast milk, comprising at least one oligonucleotide that specifically hybridizes to a SLC30A2 polynucleotide as set forth in SEQ ID NO: 1.

In some embodiments, the kit comprises at least one oligonucleotide with at least 70% homology to at least one sequence selected from the group consisting of: GATCCTGGTGTTGATGGATGCT (SEQ ID NO: 6), TGAGCAGTCAGTCTGAGGGGC (SEQ ID NO: 7), CCAAGGGCGTTGACTTCACA (SEQ ID NO: 8) and GATGTGGACAGACAGAACAGGCTGG (SEQ ID NO: 9). In some embodiments, the kit comprises at least one oligonucleotide comprising at least one sequence selected from the group consisting of: GATCCTGGTGTTGATGATGCT (SEQ ID NO: 6), TGAGCAGTCAGTCTGAGGGGC (SEQ ID NO: 7), CCAAGGGCGTTGACTTCACA (SEQ ID NO: 8) and GATGTGGACAGACAGAACAGGCTGG (SEQ ID NO: 9). In some embodiments, the kit comprises an oligonucleotide with at least 70% homology to the sequence GATCCTGGTGTTGATGGATGCT (SEQ ID NO: 6). In some embodiments, the kit comprises an oligonucleotide comprising the sequence GATCCTGGTGTTGATGGATGCT (SEQ ID NO: 6). In some embodiments, the kit comprises an oligonucleotide with at least 70% homology to the sequence CCAAGGGCGTTGACTTCACA (SEQ ID NO: 8). In some embodiments, the kit comprises an oligonucleotide comprising the sequence CCAAGGGCGTTGACTTCACA (SEQ ID NO: 8).

In some embodiments, the kit is for use in diagnosing TNZD in an infant.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
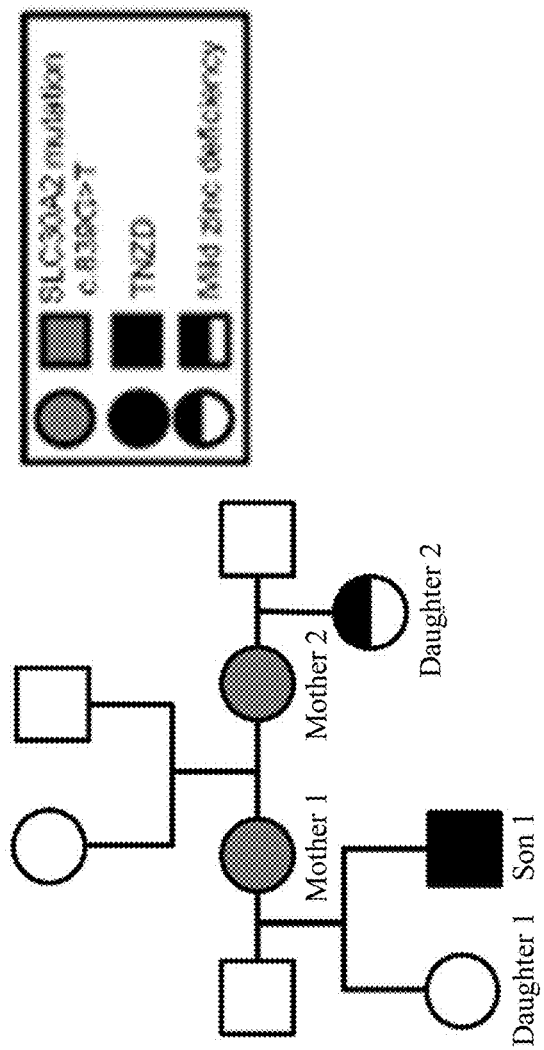
FIGS. 1A-1E describe the distinct impact of a single nucleotide mutation at the genomic level on the expressed RNA and protein levels. (1A) is a pedigree showing the family relations between patients. (1B) is a photo of a facial rash of Son 1 at the age of 13 weeks. (1C) is a chromatograph of SLC30A2/ZnT2 DNA sequencing results from Mother 1. The point mutation at position 839 is marked by an arrow. (1D) is a chromatograph of SLC30A2/ZnT2 mRNA sequencing results from Mother 1. The arrow indicates the beginning of the double sequence (i.e. WT and mutant sequence), as a result of the 27-nucleotide deletion. (1E) is an amino acid sequence showing the wild type region (upper sequence, SEQ ID NO: 14) and the corresponding region of the 9-amino acid truncation (A9AA; lower sequence, SEQ ID NO: 15).

The present invention provides, in some embodiments, methods for evaluating zinc levels in a composition comprising milk, and kits for evaluating the same, as well as methods for reducing the risk of a zinc deficiency in a subject consuming composition comprising milk. In one embodiment, the present invention provides a method for indirectly assessing a zinc deficiency or low-zinc content in a composition comprising a bodily fluid. In one embodiment, the present invention provides a method for indirectly ex-vivo assessing a zinc deficiency or low-zinc content in a composition comprising a bodily fluid such as but not limited to breast milk. In one embodiment, evaluating zinc levels is indirectly evaluating, measuring and or assessing zinc content or zinc concentration.

In one embodiment, evaluating zinc levels is indirectly evaluating, measuring and or assessing zinc content or zinc concentration via the detection of mutations in a zinc transporter or impaired expression of a zinc transporter. In one embodiment, evaluating zinc levels is indirectly evaluating, measuring and or assessing zinc content or zinc concentration via the measurement of expression of a mutant zinc binding protein or a mutant zinc carrier. In one embodiment, evaluating zinc levels is indirectly evaluating, measuring and or assessing zinc content or zinc concentration via the measurement of a mutated form of a zinc transporter or a zinc carrier. In one embodiment, measurement of a mutated form of a zinc transporter or a zinc carrier is measuring the concentration or the amount of a mutated form of a zinc transporter or zinc carrier. In one embodiment, measurement of a mutant form of a zinc transporter or a zinc carrier is determining the ratio between wild-type zinc transporter or carrier and a mutated form of the same zinc transporter or carrier.

By one aspect, the present invention concerns a method for evaluating zinc levels in a breast milk, comprising: providing a composition comprising breast milk, and screening for a mutation in a SLC30A2 polynucleotide, wherein detection of a mutation in the SLC30A2 polynucleotide, indicates that a breast milk has a low zinc content, thereby evaluating zinc levels in a breast milk.

By one aspect, the present invention concerns a method for reducing the risk of zinc deficiency in a breastfed infant, comprising: providing a composition comprising breast milk, and screening for a mutation in a SLC30A2 polynucleotide, wherein detection of a mutation in the SLC30A2 polynucleotide, indicates that a composition has a low zinc content, thereby reducing the risk of zinc deficiency in the breastfed infant.

In another embodiment, the methods and kits of the invention are for use in diagnosing TNZD in an infant.

Evaluating Zinc Levels

The terms "evaluating", "measuring", and "determining" are used interchangeably and include both quantitative and qualitative determinations. These terms refer to any form of measurement, and include determining if a characteristic, trait, or feature is present or not. The terms "evaluating," "measuring," and "determining", in some embodiments, refer to indirectly evaluating, indirectly measuring, and indirectly determining.

In some embodiments, the composition comprising milk, consists of milk. In some embodiments, the composition comprises milk and a food additive, such as but not limited to: vitamin D, vitamin A, calcium or magnesium for example. The composition comprising milk does not have zinc as an additive, and the only source of zinc in the composition is the milk. In some embodiments, the composition comprises another edible liquid or compound.

It should be well understood that milk is only produced by mammals and thus refers to any liquid produced by the mammary gland of a mammal. Such liquid is generally for feeding the animal's young, however, milk of any animal can be consumed by humans. In some embodiments, the milk is human milk. As used herein, the terms "human milk" and "breastmilk" are used interchangeably. In some embodiments, the milk is cow's milk. In some embodiments, the milk is goat's milk. In some embodiments, the milk is sheep's milk. In some embodiments, the milk is from a domesticated animal. In some embodiments, the milk is from a wild animal.

One of skill in the art will readily recognize that milk is formulated as to be sufficient nourishment for an infant without any supplementation of other nutrients. Thus, all milk, regardless of the species of origin, is naturally not zinc-deficient. In some embodiments, "not zinc-deficient" refers to having zinc in a concentration at least as high as that found in the milk of healthy human mothers. In some embodiments, "not zinc-deficient" refers to having zinc in a concentration at least as high as that found in the milk of healthy mothers of the species that produced the milk, i.e. cow milk will be not-zinc deficient if it has a concentration of zinc at least as high as that found in the milk of healthy cow mothers. In some embodiments, "not zinc-deficient" refers to 44-136 µg zinc/dL of milk or composition comprising milk. In some embodiments, "not zinc-deficient" refers to 34-146 µg zinc/dL of milk or composition comprising milk. In some embodiments, "not zinc-deficient" refers to at least 44 µg zinc/dL of milk or composition comprising milk.

In some embodiments, a composition low in zinc, or a low zinc composition, has a concentration of zinc below the normal concentration found in the milk of healthy mothers of the species that produced the milk, i.e. cow milk will be low in zinc, or low zinc milk, if it has a concentration of zinc lower than that found in the milk of healthy cow mothers. In some embodiments, a low zinc composition has a concentration of zinc below 45, 40, 35, 30, 25, 20, 15, 10, or 5 µg zinc per dL of milk or composition comprising milk. Each possibility represents a separate embodiment of the invention. In some embodiments, a low zinc composition ranges from: 0-45, 0-40, 0-35, 0-30, 0-25, 0-20, 0-15, 0-10, 5-45, 5-40, 5-35, 5-30, 5-25, 5-20, 5-15, 5-10, 10-45, 10-40, 10-35, 10-30, 10-25, 10-20, or 10-15, µg zinc/dL of milk or composition comprising milk. Each possibility represents a separate embodiment of the invention.

In one embodiment, extracting is isolating or enriching. In one embodiment, extracting SLC30A2 mRNA is isolating or enriching a sample for mRNA molecules. In one embodiments, extracting is isolating or enriching total RNA from the composition. In some embodiments, extracting is isolating or enriching total mRNA from the composition. In some embodiments, extracting is isolating or enriching SLC30A2 mRNA. In some embodiments, extracting comprises PCR of the SLC30A2 gene or mRNA.

In some embodiments, extracting SLC30A2 mRNA from a composition comprising milk comprises extracting epithelial cells. In some embodiments, the mRNA is extracted from these cells. In some embodiments, a composition comprising milk according to the invention is a composition comprising a breast cell. In some embodiments, a composition comprising milk according to the invention is a composition comprising a breast epithelial cell. In some embodiments, a composition comprising milk according to the invention is a composition comprising a white blood cell. In some embodiments, the mRNA is extracted from milk fat globules. In some embodiments, the milk fat globules contain mRNA from breast cells, breast epithelial cells, or white blood cells.

In some embodiments, the DNA or mRNA are extracted directly from the milk. In some embodiments, the epithelial cells are lysed, and the DNA or mRNA are extracted from the lysate. Extraction of DNA or mRNA from biological sources, such as cells, tissue, blood, urine and milk are well known to those skilled in the art. Several kits for performing this extraction are also commercially available, including but not limited to: Trizol (ThermoFisher), TriReagent (Sigma-Aldrich), RNeasy kits (Qiagen), QIAamp RNA blood kit (Qiagen), PureLink Genomic DNA Mini Kit (ThermoFisher) and DNeasy Blood & Tissue Kits (Qiagen).

In some embodiments, the sequence of the SLC30A2 gene comprises the variant 1 sequence, containing 8 exons. In some embodiments, the sequence of the SLC30A2 gene comprises the variant 2 sequence, containing 7 exons. In some embodiments, the sequence of the SLC30A2 gene comprises the NCBI reference sequence NM_001004434.2. In some embodiments, the coding sequence of the SLC30A2 gene comprises the following sequence:

```
                                              (SEQ ID NO: 1)
ATGGAGGCCAAGGAGAAGCAGCATCTGTTGGACGCCAGGCCGGCAATCCG

GTCATACACGGGATCTCTGTGGCAGGAAGGGGCTGGCTGGATTCCTCTGC

CCCGACCTGGCCTGGACTTGCAGGCCATTGAGCTGGCTGCCCAGAGCAAC

CATCACTGCCATGCTCAGAAGGGTCCTGACAGTCACTGTGACCCCAAGAA

GGGGAAGGCCCAGCGCCAGCTGTATGTAGCCTCTGCCATCTGCCTGTTGT
```

-continued

TCATGATCGGAGAAGTCGTTGGTGGGTACCTGGCACACAGCTTGGCTGTC

ATGACTGACGCAGCACACCTGCTCACTGACTTTGCCAGCATGCTCATCAG

CCTCTTCTCCCTCTGGATGTCCTCCCGGCCAGCCACCAAGACCATGAACT

TTGGCTGGCAGAGAGCTGAGATCTTGGGAGCCCTGGTCTCTGTACTGTCC

ATCTGGGTCGTGACGGGGGTACTGGTGTACCTGGCTGTGGAGCGGCTGAT

CTCTGGGGACTATGAAATTGACGGGGGGACCATGCTGATCACGTCGGGCT

GCGCTGTGGCTGTGAACATCATAATGGGGTTGACCCTTCACCAGTCTGGC

CATGGGCACAGCCACGGCACCACCAACCAGCAGGAGGAGAACCCCAGCGT

CCGAGCTGCCTTCATCCATGTGATCGGCGACTTTATGCAGAGCATGGGTG

TCCTAGTGGCAGCCTATATTTTATACTTCAAGCCAGAATACAAGTATGTA

GACCCCATCTGCACCTTCGTCTTCTCCATCCTGGTCCTGGGGACAACCTT

GACCATCCTGAGAGATGTGATCCTGGTGTTGATGGAAGGGACCCCCAAGG

GCGTTGACTTCACAGCTGTTCGTGATCTGCTGCTGTCGGTGGAGGGGGTA

GAAGCCCTGCACAGCCTGCATATCTGGGCACTGACGGTGGCCCAGCCTGT

TCTGTCTGTCCACATCGCCATTGCTCAGAATACAGACGCCCAGGCTGTGC

TGAAGACAGCCAGCAGCCGCCTCCAAGGGAAGTTCCACTTCCACACCGTG

ACCATCCAGATCGAGGACTACTCGGAGGACATGAAGGACTGTCAGGCATG

CCAGGGCCCCTCAGACTG.

In some embodiments, the coding sequence of the SLC30A2 gene comprises the following sequence:

(SEQ ID NO: 13)
GGCCGCGGGGCGCAGCGGCTGACCCGAGACACGGGAGCGCTTGGCACGCG

GAGCCAGAGCCGGAGCTGCAGCCGCAGCGGGAGCCGGGGGAGCTCAGGGG

CCGCAGGAGCCGGGCCGGAGTGAGCGCACCTCGCGGGGCCCTCGGGGCAG

GTGGGTGAGCGCCACCCGGAGTCCCGCGCGCAACTTTCAGGGCGCACTCG

GCGGGGCGGCTGCGCGGCTGCCGGGACTCGGCGCGGGACTGCATGGAGGC

CAAGGAGAAGCAGCATCTGTTGGACGCCAGGCCGGCAATCCGGTCATACA

CGGGATCTCTGTGGCAGGAAGGGGCTGGCTGGATTCCTCTGCCCCGACCT

GGCCTGGACTTGCAGGCCATTGAGCTGGCTGCCCAGAGCAACCATCACTG

CCATGCTCAGAAGGGTCCTGACAGTCACTGTGACCCCAAGAAGGGGAAGG

CCCAGCGCCAGCTGTATGTAGCCTCTGCCATCTGCCTGTTGTTCATGATC

GGAGAAGTCGTTGGTGGGTACCTGGCACACAGCTTGGCTGTCATGACTGA

CGCAGCACACCTGCTCACTGACTTTGCCAGCATGCTCATCAGCCTCTTCT

CCCTCTGGATGTCCTCCCGGCCAGCCACCAAGACCATGAACTTTGGCTGG

CAGAGAGCTGAGATCTTGGGAGCCCTGGTCTCTGTACTGTCCATCTGGGT

CGTGACGGGGGTACTGGTGTACCTGGCTGTGGAGCGGCTGATCTCTGGGG

ACTATGAAATTGACGGGGGGACCATGCTGATCACGTCGGGCTGCGCTGTG

GCTGTGAACATCATAATGGGGTTGACCCTTCACCAGTCTGGCCATGGGCA

CAGCCACGGCACCACCAACCAGCAGGAGGAGAACCCCAGCGTCCGAGCTG

CCTTCATCCATGTGATCGGCGACTTTATGCAGAGCATGGGTGTCCTAGTG

GCAGCCTATATTTTATACTTCAAGCCAGAATACAAGTATGTAGACCCCAT

CTGCACCTTCGTCTTCTCCATCCTGGTCCTGGGGACAACCTTGACCATCC

TGAGAGATGTGATCCTGGTGTTGATGGAAGGGACCCCCAAGGGCGTTGAC

TTCACAGCTGTTCGTGATCTGCTGCTGTCGGTGGAGGGGGTAGAAGCCCT

GCACAGCCTGCATATCTGGGCACTGACGGTGGCCCAGCCTGTTCTGTCTG

TCCACATCGCCATTGCTCAGAATACAGACGCCCAGGCTGTGCTGAAGACA

GCCAGCAGCCGCCTCCAAGGGAAGTTCCACTTCCACACCGTGACCATCCA

GATCGAGGACTACTCGGAGGACATGAAGGACTGTCAGGCATGCCAGGGCC

CCTCAGACTGACTGCTCAGCCAGGCACCAACTGGGGCATGAACAGGACCT

GCAGGTGGCTGGACTGAGTGTCCCCCAGGCCCAGCCAGGACTTTGCCTAC

CCCAGCTGTGTTGTAAACCAGGTCCCCCTCCTGACCTCTGCCCCACTCCA

GGAATGGAGCTCTTCCCAGCCTCCCATCTGACTACAGCCAGGGTGGGGAC

TCAGCGGGTATAAAGCTAGTGTGACCCTGCTCTTCCAGCTCCTGGGCCAG

CTCTGGAAGGGCTGTATTTGGGCCTAATCCTCAGCAAATGTTCTACCACT

CGCAGGGGCAAAGGTGGTGAGCCACGGGACGTCCAAGGGGAGGCTGGCCC

CAGCGCGCCCATACTGCCTGCCTCATGCCCCATTCTCAGCCTGGCTGGCC

TTTGCCTTTATGAATCTGAGCCCCTCCATCTGCCTATAGCAATAGGCACG

GGGGTGAGGACCCTCACACTCTCATTTGAGCCTCCCTGAGGCAGGGAGCC

AGGAGGCACCTGAGGCCTATCTGTGCCTTAGTCACTTCAGCTATGAGCCA

AATGTTCCCTTTCCTGGAGGGGAGAGGCTTCTTACTAGGTAAGAGACAGG

TTTCCTCTTT.

In some embodiments, the SLC30A2 mRNA sequence or cDNA generated from the mRNA sequence are at least 99, 95, 90, 85, 80, 75, or 70% identical to the sequence provided in SEQ ID NO: 1. Each possibility represents a separate embodiment of the invention. In some embodiments, the SLC30A2 mRNA sequence or cDNA generated from the mRNA sequence is at least 99, 95, 90, 85, 80, 75, or 70% homologous to the sequence provided in SEQ ID NO: 1. Each possibility represents a separate embodiment of the invention. In some embodiments, the SLC30A2 mRNA sequence or cDNA generated from the mRNA sequence comprise the sequence presented in SEQ ID NO:1, but with 1, 2, 3, 4, 5, 6, 7, 8, 9, 10 or more synonymous mutations that do not affect the protein coded for by the mRNA. Each possibility represents a separate embodiment of the invention. In some embodiments, the SLC30A2 mRNA sequence or cDNA generated from the mRNA sequence consist of the sequence presented in SEQ ID NO:1. In some embodiments, the SLC30A2 mRNA sequence or cDNA generated from the mRNA sequence is the sequence presented in SEQ ID NO:1.

In some embodiments, a homolog of SLC30A2 is at least 99, 95, 90, 85, 80, 75, or 70% homologous to the sequence provided in SEQ ID NO: 1. Each possibility represents a separate embodiment of the invention. In some embodiments, a homolog of SLC30A2, is the SLC20A2 gene or mRNA from a species other than humans. In some embodiments, a homolog of SLC30A2, is the SLC20A2 gene or mRNA from a mammalian species other than humans. Homologs of genes, mRNAs and proteins from species other than humans are well known to those skilled in the art, and can be found on, or by using, websites such as www.ncbi.nlm.nih.gov/homologene, www.ncbi.nlm.nih.gov/nuccore, and blast.ncbi.nlm.nih.gov/Blast.cgi to name a few non-limiting examples.

Extracting polynucleotides, e.g., DNA, mRNA, etc. from biological samples is well known to those skilled in the art. General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998).

SLC30A2 Mutations

In some embodiments, the mutation in SLC30A2 gene reduces stability of the mRNA, or reduces translation of the mRNA. Reduction in mRNA stability, increased degradation of the mRNA, such as by nonsense-mediated mRNA decay for example, or inhibition of translation will result in less ZnT2 protein being produced. In some embodiments, the mutation in SLC30A2 gene that is transcribed into the SLC30A2 mRNA reduces the level of ZnT2 protein produced.

As used herein, the terms "reducing" and "decreasing" are used interchangeably to refer to a statistically significant reduction in the stability of the mRNA, translation/expression of the protein, homodimerization or zinc transport. In one embodiment, reduction refers to a reduction of at least 30%, or alternatively at least 40%, or alternatively at least 50%, or alternatively at least 60%, or alternatively at least 70%, or alternatively at least 75%, or alternatively at least 80%, or alternatively at least 85%, or alternatively at least 90%, or alternatively at least 95%, or alternatively at least 97% or alternatively at least 99% reduction in expression and/or activity. Each possibility represents a separate embodiment of the present invention.

Decreased ZnT2 protein levels cause a reduction in zinc deposition in produced milk. In some embodiments, the mutant SLC30A2 mRNA produces less ZnT2 protein that the wild-type SLC30A2 mRNA. In some embodiments, the mutant SLC30A2 mRNA produces less than 10, 20, 30, 40, 50, 60, 70, 80, 90, 95, or 99% of the ZnT2 protein that the wild-type SLC30A2 mRNA produces. Each possibility represents a separate embodiment of the current invention. In some embodiments, the mutant SLC30A2 mRNA produces no ZnT2 protein.

In some embodiments, the mutation in SLC30A2 mRNA reduces homodimerization of ZnT2 protein produced, reduces zinc binding by ZnT2 protein produced or reduces zinc transport by ZnT2 protein produced. ZNT2 requires homodimerization in order to bind zinc molecules. Loss of transport of zinc by ZnT2 results in reduced zinc secretion into the produced milk. In one embodiment, reduction refers to a reduction of at least 30%, or alternatively at least 40%, or alternatively at least 50%, or alternatively at least 60%, or alternatively at least 70%, or alternatively at least 75%, or alternatively at least 80%, or alternatively at least 85%, or alternatively at least 90%, or alternatively at least 95%, or alternatively at least 97% or alternatively at least 99% reduction in homodimerization. In some embodiments, the mutant SLC30A2 mRNA produces protein that homodimerizes at less than 1, 5, 10, 20, 30, 40, 50, 60, 70, 80, or 90% of the frequency that the ZnT2 protein produced by the wild-type SLC30A2 mRNA does. Each possibility represents a separate embodiment of the current invention. In some embodiments, the mutant SLC30A2 mRNA produces protein that does not homodimerize at all.

In some embodiments, the mutant SLC30A2 mRNA produces protein that binds zinc at less than 1, 5, 10, 20, 30, 40, 50, 60, 70, 80, or 90% of the efficiency that ZnT2 protein produced by the wild-type SLC30A2 mRNA does. Each possibility represents a separate embodiment of the current invention.

In one embodiment, reduced zinc binding refers to a reduction of at least 30%, or alternatively at least 40%, or alternatively at least 50%, or alternatively at least 60%, or alternatively at least 70%, or alternatively at least 75%, or alternatively at least 80%, or alternatively at least 85%, or alternatively at least 90%, or alternatively at least 95%, or alternatively at least 97% or alternatively at least 99% reduction in zinc transport. Each possibility represents a separate embodiment of the current invention. In some embodiments, the mutant SLC30A2 mRNA produces protein that does not bind zinc at all.

In some embodiments, the mutant SLC30A2 mRNA produces protein that transports zinc at less than 1, 5, 10, 20, 30, 40, 50, 60, 70, 80, or 90% of the efficiency that ZnT2 protein produced by the wild-type SLC30A2 mRNA does. Each possibility represents a separate embodiment of the current invention.

In one embodiment, reduced zinc transport refers to a reduction of at least 30%, or alternatively at least 40%, or alternatively at least 50%, or alternatively at least 60%, or alternatively at least 70%, or alternatively at least 75%, or alternatively at least 80%, or alternatively at least 85%, or alternatively at least 90%, or alternatively at least 95%, or alternatively at least 97% or alternatively at least 99% reduction in zinc transport. Each possibility represents a separate embodiment of the current invention. In some embodiments, the mutant SLC30A2 mRNA produces protein that does not transport zinc at all. In some embodiments, the mutation in SLC30A2 mRNA produces a combination at least 2, 3, 4, 5, or all of the results described above. Each possibility represents a separate embodiment of the current invention.

In some embodiments, the mutation is selected from the group consisting of: mutation of adenine 161, mutation of guanine 259, mutation of thymine 454, deletion of cytosine 663, mutation of guanine 838, mutation of guanine 839, deletion of bases 840-866, mutation of cytosine 887, mutation of cytosine 935, and mutation of guanine 1,063. The numbering of the base pairs is relative to the ATG translational start codon of SLC30A2 as provided in SEQ ID NO: 1. It will be well understood by one skilled in the art that the DNA will contain thymine and mRNA will contain uracil bases, and when the mRNA is reverse transcribed to cDNA it will contain thymine bases. In some embodiments, guanine 839 is mutated to thymine. In some embodiments, mutation of guanine 839 to thymine (G839T) in the gene body will result in an mRNA in which bases 840-866 have been deleted. In some embodiments, cytosine 839 is mutated to adenine. In some embodiments, mutation of cytosine 839 to adenine (C839A) in the gene body will result in an mRNA in which bases 840-866 have been deleted.

Screening

In some embodiments, screening for a mutation comprises detecting the mutation. In some embodiments, screening for a mutation comprises detecting wilt-type DNA or mRNA. In some embodiments, cDNA is generated from mRNA by means of reverse transcription. In some embodiments, screening for a mutation comprises sequencing the DNA or cDNA. Sequencing of nucleic acids is well known to those skilled in the art, and as used herein refers to reading all the base pairs that comprise the DNA or cDNA. In some embodiments, sequencing the DNA or cDNA comprises the DNA or RNA-Seq technique. In some embodiments, sequencing comprises high-throughput sequencing. In some embodiments, sequencing comprises Sanger sequencing. Methods of sequencing can be found in the molecular biology textbooks listed above. In some embodiments, sequencing comprises sequencing with gene-specific primers.

As used herein, the term "primer" includes an oligonucleotide, either natural or synthetic, that is capable, upon forming a duplex with a polynucleotide template, of acting as a point of initiation of nucleic acid synthesis and being extended from its 3' end along the template so that an extended duplex is formed. Primers within the scope of the present invention bind adjacent to a target sequence. A "primer" may be considered a short polynucleotide, generally with a free 3'-OH group that binds to a target or template potentially present in a sample of interest by hybridizing with the target, and thereafter promoting polymerization of a polynucleotide complementary to the target. Primers of the invention are comprised of nucleotides ranging from 8 to 30 nucleotides. In one aspect, the primer is at least 8, 9, 10, 11, 12, 13, 14, 15, 16, 17, 18, 19, 20, 21, 22, 23, 24, 25, 26, 27, 28, 29, or 30 nucleotides. Each possibility represents a separate embodiment of the invention. In one embodiment, the primer is at most 40, 50, 75 or 100 nucleotides. Each possibility represents a separate embodiment of the invention.

A gene-specific primer, as used herein, is therefore a primer that forms a duplex with only the gene or mRNA of interest. Design of gene-specific primers will be well known to those skilled in the art and such primers can be found or designed on various websites such as http://bioinfo.ut.ee/primer3-0.4.0/ or https://pga.mgh.harvard.edu/primerbank/ for example.

In some embodiments, the sequencing employs at least one primer with at least 70% homology to at least one sequence selected from the group consisting of: ACTGCATGGAGGCCAAGGAG (SEQ ID NO: 2), GTCGCCGATCACATGGATG (SEQ ID NO: 3), CTGGTGTACCTGGCTGTGGAG (SEQ ID NO: 4), or TGAGCAGTCAGTCTGAGGGGC (SEQ ID NO: 5). In some embodiments, the sequencing employs at least one primer with at least 70, 75, 80, 85, 90, 95, or 99% homology to at least one of SEQ ID NO: 2, SEQ ID NO: 3, SEQ ID NO: 4, or SEQ ID NO: 5. Each possibility represents a separate embodiment of the current invention.

In some embodiments, the sequencing employs at least one primer comprising at least one sequence selected from the group consisting of: ACTGCATGGAGGCCAAGGAG (SEQ ID NO: 2), GTCGCCGATCACATGGATG (SEQ ID NO: 3), CTGGTGTACCTGGCTGTGGAG (SEQ ID NO: 4), or TGAGCAGTCAGTCTGAGGGGC (SEQ ID NO: 5). In some embodiments, the sequencing employs at least one primer consisting of at least one sequence selected from the group consisting of: ACTGCATGGAGGCCAAGGAG (SEQ ID NO: 2), GTCGCCGATCACATGGATG (SEQ ID NO: 3), CTGGTGTACCTGGCTGTGGAG (SEQ ID NO: 4), or TGAGCAGTCAGTCTGAGGGGC (SEQ ID NO: 5).

In some embodiments, screening for a mutation comprises PCR analysis of DNA. In some embodiments, a DNA polynucleotide comprises a cDNA polynucleotide generated from a mRNA polynucleotide. Reverse transcription of mRNA into cDNA as well PCR analysis will be well known to one skilled in the art. Many commercial kits are available for making cDNA, including, but not limited to: the high-capacity RNA-to-cDNA kit (ThermoFisher), the iScript advanced cDNA synthesis kit (Bio-Rad), and the universal riboclone cDNA synthesis system (Promega), to name but a few. In some embodiments, PCR analysis comprises running the PCR product on an agarose gel. In some embodiments, PCR analysis comprises sequencing the PCR product. In some embodiments, PCR analysis comprises real-time or quantitative PCR analysis of the levels of the mRNA present. In some embodiments, PCR analysis comprises a comparative analysis of the levels of a wild-type mRNA and a mutant mRNA.

In some embodiments, the PCR analysis employs a primer with at least 70% homology to the sequence GATCCTGGTGTTGATGGATGCT (SEQ ID NO: 6). The sequence provided in SEQ ID NO:6 spans the junction on exon 6 and the truncated exon 7 formed when bases 840-866 of SLC30A2 are deleted. In some embodiments, the PCR analysis employs a primer with at least 70, 75, 80, 85, 90, 95, or 99% homology to the sequence GATCCTGGTGTTGATGGATGCT (SEQ ID NO: 6). Each possibility represents a separate embodiment of the current invention. In some embodiments, the PCR analysis employs a primer comprising the sequence GATCCTGGTGTTGATGGATGCT (SEQ ID NO: 6). In some embodiments, the PCR analysis employs a primer consisting of the sequence GATCCTGGTGTTGATGGATGCT (SEQ ID NO: 6).

In some embodiments, the PCR analysis employs a primer with at least 70% homology to the sequence TGAGCAGTCAGTCTGAGGGGC (SEQ ID NO: 7). The sequences in SEQ ID NO: 6 and 7, when employed together for PCR analysis, will produce a PCR product 281 base pairs in length, if the G839T mutation is present in the DNA or mRNA. The sequences in SEQ ID NO: 6 and 7, when employed together for PCR analysis, will produce a PCR product 281 base pairs in length, if the C839A mutation is present in the DNA or mRNA. In some embodiments, the PCR analysis employs a primer that spans the junction of exon 6 and the truncated exon 7 of the mutant SLC30A2 gene or its product. In some embodiments, the PCR analysis produces a product that spans bases 840-866 of the SLC30A2 gene or its mRNA product. In some embodiments, the PCR analysis spans bases 840-866. In some embodiments, the PCR analysis employs a primer with at least 70, 75, 80, 85, 90, 95, or 99% homology to the sequence TGAGCAGTCAGTCTGAGGGGC (SEQ ID NO: 7). Each possibility represents a separate embodiment of the current invention. In some embodiments, the PCR analysis employs a primer comprising the sequence TGAGCAGTCAGTCTGAGGGGC (SEQ ID NO: 7). In some embodiments, the PCR analysis employs a primer consisting of the sequence TGAGCAGTCAGTCTGAGGGGC (SEQ ID NO: 7).

In some embodiments, the PCR analysis employs a primer with at least 70% homology to the sequence CCAAGGGCGTTGACTTCACA (SEQ ID NO: 8). The sequence provided in SEQ ID NO:8 is within the 27 bp that are deleted when the G839T mutation is present in the gene or the cDNA generated from its mRNA product. The sequence provided in SEQ ID NO:8 is within the 27 bp that are deleted when the C839A mutation is present in the gene or its mRNA product. In some embodiments, the PCR analysis employs a primer with at least 70, 75, 80, 85, 90, 95, or 99% homology to the sequence CCAAGGGCGTTGACTTCACA (SEQ ID NO: 8). Each possibility represents a separate embodiment of the current invention. In some embodiments, the PCR analysis employs a primer comprising the sequence CCAAGGGCGTTGACTTCACA (SEQ ID NO: 8). In some embodiments, the PCR analysis employs a primer consisting of the sequence

CCAAGGGCGTTGACTTCACA.    (SEQ ID NO: 8)

In some embodiments, the PCR analysis employs a primer with at least 70% homology to the sequence GATGTGGACAGACAGAACAGGCTGG (SEQ ID NO: 9). The sequences in SEQ ID NO: 8 and 9, when employed together for PCR analysis, will produce a PCR product 95 base pairs in length, if the G839T mutation is not present in the gene or the cDNA generated from its mRNA product. In some embodiments, the PCR analysis employs a primer that hybridizes to at least 1, 2, 3, 4, 5, 6, 7, 8, 9, 10, 11, 12, 13, 14, 15 or more base pairs within the 27 bp region missing from a gene or cDNA generated from its mRNA product containing the G839T mutation. Each possibility represents a separate embodiment of the current invention. The sequences in SEQ ID NO: 8 and 9, when employed together for PCR analysis, will produce a PCR product 95 base pairs in length, if the C839A mutation is not present in the gene or its mRNA product. In some embodiments, the PCR analysis employs a primer that hybridizes to at least 1, 2, 3, 4, 5, 6, 7, 8, 9, 10, 11, 12, 13, 14, 15 or more base pairs within the 27 bp region missing from a gene or its mRNA product containing the C839A mutation. Each possibility represents a separate embodiment of the current invention. In some embodiments, the PCR analysis employs a primer than spans the junction of exon 6 and 7 of the SLC30A2 gene or its product. In some embodiments, the PCR analysis employs a primer with at least 70, 75, 80, 85, 90, 95, or 99% homology to the sequence GATGTGGACA-GACAGAACAGGCTGG (SEQ ID NO: 9). Each possibility represents a separate embodiment of the current invention. In some embodiments, the PCR analysis employs a primer comprising the sequence GATGTGGACA-GACAGAACAGGCTGG (SEQ ID NO: 9). In some embodiments, the PCR analysis employs a primer consisting of the sequence

GATGTGGACAGACAGAACAGGCTGG.    (SEQ ID NO: 9)

Reducing Zinc Deficiency Risk

In some embodiments, zinc deficiency is a condition of below normal zinc levels in a subject's blood. In some embodiments, normal levels of zinc in the blood range from 55 to 165 µg/dL. In some embodiments, zinc deficiency has symptoms including, but not limited to, an erythematous scaly rash. In some embodiments, the skin rash can be mild, moderate or severe. In some embodiments, the rash can present in the face, neck, or diaper area. In some embodiments, zinc deficiency is asymptomatic. In some embodiments, zinc deficiency comprises blood zinc levels below 55, 50, 45, 40, 35, or 30 µg/dL. Each possibility represents a separate embodiment of the invention. In some embodiments, zinc deficiency comprises concentration of zinc in the blood between 0-55, 0-50, 0-45, 0-40, 0-35, 0-30, 0-25, 0-20, 0-15, 0-10, 5-55, 5-50, 5-45, 5-40, 5-35, 5-30, 5-25, 5-20, 5-15, 5-10, 10-55, 10-50, 10-45, 10-40, 10-35, 10-30, 10-25, 10-20, or 10-15, µg zinc/dL of blood. Each possibility represents a separate embodiment of the invention.

The terms "risk of a zinc deficiency" and "risk of acquiring a zinc deficiency", are used herein interchangeably, and refer to a likelihood of the subject's blood-zinc concentration dropping below healthy levels due to consumption of below normal levels of dietary zinc. In some embodiments, reducing the risk of a zinc deficiency comprises the subject not consuming a low zinc composition. In some embodiments, not consuming a low zinc composition comprises supplementing the composition with zinc such that it is no long a low zinc composition. In some embodiments, reducing the risk of a zinc deficiency comprises the subject not consuming a low zinc composition as the subject's only source of dietary zinc.

In some embodiments, a subject diagnosed with a risk of a zinc deficiency is supplemented with zinc. In some embodiments, a subject diagnosed with a risk of a zinc deficiency is given a composition comprising milk that has been supplemented with zinc. In some embodiments, a subject diagnosed with a risk of a zinc deficiency is proscribed zinc supplements. In some embodiments, a subject diagnosed with a risk of a zinc deficiency is instructed not to consume a composition low in zinc.

In some embodiments, the methods of the invention further comprise diagnosing transient neonatal zinc deficiency (TNZD) in a subject or reducing the risk of acquiring TNZD in a subject, wherein the subject is an infant, and wherein detection of a mutation in SLC30A2 mRNA determines that the infant suffers from TNZD. In some embodiments, the composition comprising milk is consumed, has been consumed, or is to be consumed, by an infant and the methods of the invention further comprise diagnosing TNZD in the infant, wherein detection of the mutation determines the infant is afflicted with TNZD.

As used herein, the term "diagnosis" means detecting a disease or disorder or determining the stage, severity or degree of a disease or disorder, distinguishing a disease from other diseases including those diseases that may feature one or more similar or identical symptoms, as well as selecting a therapy and/or a treatment for a disease, optimization of a given therapy for a disease, monitoring the treatment of a disease, and/or predicting the suitability of a therapy for specific patients or subpopulations or determining the appropriate dosing of a therapeutic product in patients or subpopulations. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative of the diagnosis of a particular disease does not need to be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder, e.g., TNZD.

In some embodiments, diagnosing TNZD distinguishes it from a skin ailment. Mild TNZD can be asymptomatic. In some embodiments, diagnosing TNZD determines the severity of the condition. In some embodiments, diagnosing TNZD is accompanied by direct measurement of the zinc concentration in the infant's blood. In some embodiments, diagnosing TNZD determines the method of treatment, for instance zinc supplements administered to the infant or into the composition comprising milk. In some embodiments, diagnosing TNZD determines the dosing regimen, i.e. how much zinc to give to the infant.

In some embodiments, the subject consuming a composition comprising milk is an infant. In some embodiments, the infant is a human infant. In some embodiments, the infant is a domesticated animal. In some embodiments, the infant is an infant farm animal. In some embodiments, the infant is breastfed. In some embodiments, the infant is bottle-fed. In some embodiments, the infant is fed breastmilk, either from the breast or from a bottle. In some embodiments, the composition comprising milk is the infant's only source of dietary zinc. In some embodiments, the milk in the composition comprising milk is the infant's only source of dietary zinc.

In some embodiments, the methods of diagnosing TNZD further comprise treating TNZD by administering zinc to the infant. In some embodiments, the zinc is administered orally to the infant. In some embodiments, the zinc is administered to the composition comprising milk to be consumed by the infant.

Kits

In some embodiments, the disclosed invention comprises a kit for evaluating zinc levels in a composition comprising milk, comprising at least one oligonucleotide that specifically hybridizes to a SLC30A2 polynucleotide as set forth in SEQ ID NO: 1.

The terms "primer" and "oligonucleotide", are used herein interchangeably.

The term "hybridization" or "hybridizes" as used herein refers to the formation of a duplex between nucleotide sequences which are sufficiently complementary to form duplexes via Watson-Crick base pairing. Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T (U), G and C of one sequence is then aligned with a T (U), A, C and G, respectively, of the other sequence. RNA sequences can also include complementary G=U or U=G base pairs. Thus, two sequences need not have perfect homology to be "complementary" or "hybridize" under the invention.

In one embodiment, methods for visualizing the nucleic acid molecule as described herein or the amplicons generated in the PCR is gel electrophoresis in polyacrylamide or agarose, followed by ethidium bromide staining. The observed sizes of the amplified target fragment—the nucleic acid molecule as described herein, should be identical to the predicted from the known nucleotide sequence as described and exemplified. In one embodiment, methods for visualizing the nucleic acid molecule as described herein or the amplicons generated in the PCR comprises Southern blot probing, dot-blots, or any known DNA hybridization technique wherein the nucleic acid molecule as described herein is utilized as a probe.

The term "probe" refers to a labeled or unlabeled oligonucleotide capable of selectively hybridizing to a target or template nucleic acid under suitable conditions. Typically, a probe is sufficiently complementary to a specific target sequence contained in a nucleic acid sample to form a stable hybridization duplex with the target sequence under a selected hybridization condition, such as, but not limited to, a stringent hybridization condition. A hybridization assay carried out using the probe under sufficiently stringent hybridization conditions permits the selective detection of a specific target sequence. For use in a hybridization assay for the discrimination of single nucleotide differences in sequence, the hybridizing region is typically from about 8 to about 100 nucleotides in length. Although the hybridizing region generally refers to the entire oligonucleotide, the probe may include additional nucleotide sequences that function, for example, as linker binding sites to provide a site for attaching the probe sequence to a solid support or the like, as sites for hybridization of other oligonucleotides, as restriction enzymes sites or binding sites for other nucleic acid binding enzymes, etc. In certain embodiments, a probe of the invention is included in a nucleic acid that comprises one or more labels (e.g., a reporter dye, a quencher moiety, a fluorescent labeling, etc.), such as a 5'-nuclease probe, a FRET probe, a molecular beacon, or the like, which can also be utilized to detect hybridization between the probe and target nucleic acids in a sample. In some embodiments, the hybridizing region of the probe is completely complementary to the target sequence. However, in general, complete complementarity is not necessary (i.e., nucleic acids can be partially complementary to one another); stable duplexes may contain mismatched bases or unmatched bases. Modification of the stringent conditions may be necessary to permit a stable hybridization duplex with one or more base pair mismatches or unmatched bases. Sambrook et al., Molecular Cloning: A Laboratory Manual, $3^{rd}$ Ed., Cold Spring Harbor Laboratory Press, Cold Spring Harbor, N.Y. (2001), which is incorporated by reference, provides guidance for suitable modification. Stability of the target/probe duplex depends on a number of variables including length of the oligonucleotide, base composition and sequence of the oligonucleotide, temperature, and ionic conditions. One of skill in the art will recognize that, in general, the exact complement of a given probe is similarly useful as a probe. One of skill in the art will also recognize that, in certain embodiments, probe nucleic acids can also be used as primer nucleic acids. Exemplary probe nucleic acids include 5'-nuclease probes, molecular beacons, among many others known to persons of skill in the art.

As used herein, "hybridization" refers to a reaction in which at least one polynucleotide reacts to form a complex that is stabilized via hydrogen bonding between the bases of the nucleotide residues. The hydrogen bonding may occur by. Watson-Crick base pairing, in any other sequence-specific manner. A hybridization reaction may constitute a step in a more extensive process, such as the initiation of a PCR reaction.

Hybridization reactions can be performed under conditions of different stringency. Under stringent conditions, nucleic acid molecules at least 60%, 65%, 70%, 75% identical to each other remain hybridized to each other. A non-limiting example of highly stringent hybridization conditions is hybridization in 6× Sodium chloride/Sodium citrate (SSC) at approximately 45° C., followed by one or more washes in 0.2×SSC and 0.1% SDS at 50° C., at 55° C., or at about 60° C., or more.

When hybridization occurs in an anti-parallel configuration between two single-stranded polynucleotides, those polynucleotides are described as complementary.

Hybridization based assays which allow the detection of a biomarker of interest in a biological sample rely on the use of probe(s) which can be 10, 15, 20, or 30 to 100 nucleotides long optionally from 10 to 50, or from 40 to 50 nucleotides long.

Thus, the polynucleotides of the of the invention, according to at least some embodiments, are optionally hybridizable with any of the herein described nucleic acid sequences under moderate to stringent hybridization conditions.

The detection of hybrid duplexes can be carried out by several methods. Typically, hybridization duplexes are separated from unhybridized nucleic acids and the labels bound to the duplexes are then detected. Such labels refer to radioactive, fluorescent, biological or enzymatic tags or labels of standard use in the art. A label can be conjugated to either the oligonucleotide probes or the nucleic acids derived from the biological sample.

Probes can be labeled according to numerous well-known methods. Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

For example, oligonucleotides according to at least some embodiments of the present invention can be labeled subsequently to synthesis, by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, when fluorescently-labeled oligonucleotide probes are used, fluorescein, lissamine, phycoerythrin, rhodamine (Perkin Elmer Cetus), Cy2, Cy3, Cy3.5, Cy5, Cy5.5, Cy7, Fluor X (Amersham) and others (e.g., Kricka et al. (1992), Academic Press San Diego, Calif.) can be attached to the oligonucleotides. Preferably, detection of the biomarkers of the invention is achieved by using TaqMan assays, preferably by using combined reporter and quencher molecules (Roche Molecular Systems Inc.).

Although the present invention is not specifically dependent on the use of a label for the detection of a particular nucleic acid sequence, such a label might be beneficial, by increasing the sensitivity of the detection. Furthermore, it enables automation. Probes can be labeled according to numerous well-known methods.

As commonly known, radioactive nucleotides can be incorporated into probes of the invention by several methods. Non-limiting examples of radioactive labels include $^3$H, $^{14}$C, $^{32}$P, and $^{35}$S.

Those skilled in the art will appreciate that wash steps may be employed to wash away excess target polynucleotide or probe as well as unbound conjugate. Further, standard heterogeneous assay formats are suitable for detecting the hybrids using the labels present on the oligonucleotide primers and probes.

It will be appreciated that a variety of controls may be usefully employed to improve accuracy of hybridization assays. For instance, samples may be hybridized to an irrelevant probe and treated with RNase A prior to hybridization, to assess false hybridization.

Probes of the invention can be utilized with naturally occurring sugar-phosphate backbones as well as modified backbones including phosphorothioates, dithionates, alkyl phosphonates and a-nucleotides and the like. Probes of the invention can be constructed of either ribonucleic acid (RNA) or deoxyribonucleic acid (DNA).

An additional nucleic acid test (NAT) test known in the art is Fluorescence In Situ Hybridization (FISH). FISH uses fluorescent single-stranded DNA or RNA probes which are complementary to the nucleotide sequences that are under examination (genes, chromosomes, amplification products, or RNA). These probes hybridize with the complementary nucleotide and allow the identification of the sequences of DNA (for example chromosomal location of genomic polynucleotide) or RNA.

Detection of a nucleic acid of interest in a biological sample may also optionally be affected by NAT-based assays, which involve nucleic acid amplification technology, such as PCR for example (or variations thereof such as real-time PCR for example).

The terms "primer" and "oligonucleotide" are interchangeable, and used herein to define a relatively short nucleic acid polymer which is capable of annealing to (hybridizing with) a target sequence, thereby creating a double stranded region which can serve as an initiation point for DNA synthesis under suitable conditions. Although other primer nucleic acid lengths are optionally utilized, they typically comprise hybridizing regions that range from about 8 to about 100 nucleotides in length. Short primer nucleic acids generally utilize cooler temperatures to form sufficiently stable hybrid complexes with template nucleic acids. A primer nucleic acid that is at least partially complementary to a subsequence of a template nucleic acid is typically sufficient to hybridize with the template for extension to occur. A primer nucleic acid can be labeled (e.g., a SCORPION primer, etc.), if desired, by incorporating a label detectable by, e.g., spectroscopic, photochemical, biochemical, immunochemical, chemical, or other techniques. To illustrate, useful labels include radioisotopes, fluorescent dyes, electron-dense reagents, enzymes (as commonly used in ELISAs), biotin, or haptens and proteins for which antisera or monoclonal antibodies are available. Many of these and other labels are described further herein and/or otherwise known in the art. One of skill in the art will recognize that, in certain embodiments, primer nucleic acids can also be used as probe nucleic acids.

In one embodiment, the composition and/or the kit as described herein comprise a PCR buffer. In one embodiment, a PCR buffer comprises: 5 to 100 mM Tris-HCl and 20 to 100 mM KCl. In one embodiment, a PCR buffer further comprises 10 to 100 mM Magnesium Chloride. In one embodiment, the composition and/or the kit as described herein comprise a dNTP mixture. In one embodiment, the composition as described herein comprises DNA extracted from a cell. In one embodiment, the composition as described herein comprises total DNA extracted from a cell. In one embodiment, the composition as described herein comprises complementary DNA (i.e., cDNA) generated by means of reverse transcription form a mRNA molecule extracted from a cell. In one embodiment, the composition and/or the kit as described herein comprise DNA Polymerase such as but not limited to Taq DNA Polymerase. In one embodiment, the composition and/or the kit as described herein comprise distilled water. In one embodiment, the composition comprises a "PCR composition" as described herein. In one embodiment, the composition comprises a "product" as described herein.

In some embodiments, the kit comprises a primer with at least 70% homology to the sequence GATCCTGGTGTT-GATGGATGCT (SEQ ID NO: 6). In some embodiments, the kit comprises a primer with at least 70, 75, 80, 85, 90, 95, or 99% homology to the sequence GATCCTGGTGTT-GATGGATGCT (SEQ ID NO: 6). Each possibility represents a separate embodiment of the invention. In some embodiments, the kit comprises a primer comprising the sequence GATCCTGGTGTTGATGGATGCT (SEQ ID NO: 6). In some embodiments, the kit comprises a primer consisting of the sequence GATCCTGGTGTTGATGGATGCT (SEQ ID NO: 6).

In some embodiments, the kit comprises a primer with at least 70% homology to the sequence TGAGCAGTCAGTCTGAGGGGC (SEQ ID NO: 7). In some embodiments, the kit comprises a primer with at least 70, 75, 80, 85, 90, 95, or 99% homology to the sequence

```
    TGAGCAGTCAGTCTGAGGGGC.    (SEQ ID NO: 7)
```

Each possibility represents a separate embodiment of the invention. In some embodiments, the kit comprises a primer comprising the sequence TGAGCAGTCAGTCT-GAGGGGC (SEQ ID NO: 7). In some embodiments, the kit comprises a primer consisting of the sequence TGAGCAGTCAGTCTGAGGGGC (SEQ ID NO: 7).

In some embodiments, the kit comprises a primer with at least 70% homology to the sequence CCAAGGGCGTTGACTTCACA (SEQ ID NO: 8). In some embodiments, the kit comprises a primer with at least 70, 75, 80, 85, 90, 95, or 99% homology to the sequence CCAAGGGCGTTGACTTCACA (SEQ ID NO: 8). Each possibility represents a separate embodiment of the invention. In some embodiments, the kit comprises a primer comprising the sequence CCAAGGGCGTTGACTTCACA (SEQ ID NO: 8). In some embodiments, the kit comprises a primer consisting of the sequence CCAAGGGCGTTGACTTCACA (SEQ ID NO: 8).

In some embodiments, the kit comprises a primer with at least 70% homology to the sequence GATGTGGACA-GACAGAACAGGCTGG (SEQ ID NO: 9). In some embodiments, the kit comprises a primer with at least 70, 75, 80, 85, 90, 95, or 99% homology to the sequence GATGTGGACAGACAGAACAGGCTGG (SEQ ID NO: 9). Each possibility represents a separate embodiment of the invention. In some embodiments, the kit comprises a primer comprising the sequence GATGTGGACA-GACAGAACAGGCTGG (SEQ ID NO: 9). In some embodiments, the kit comprises a primer consisting of the sequence

```
    GATGTGGACAGACAGAACAGGCTGG.    (SEQ ID NO: 9)
```

In some embodiments, the kit comprises at least 1, at least 2, at least 3 or all of the above described primers. Each possibility represents a separate embodiment of the invention.

In some embodiments, the milk in the composition comprising milk is human milk. In some embodiments, the milk in the composition comprising milk is milk from a domesticated animal. In some embodiments, the milk in the composition comprising milk is cow's, goat's, or sheep's milk.

In some embodiment, a subject according to the present invention is an infant. In some embodiments, an infant is fed on milk. In some embodiments, milk is breast milk. In some embodiments, infant is fed on breast milk. In some embodiments, infant is breastfed. In some infant is fed indirectly on collected breast milk. Non-limiting example, includes but not limited to, breast milk that is collected by a pumping device and fed to an infant thereafter.

In some embodiments, the kits of the invention are for diagnosing TNZD in an infant, wherein the composition comprising milk is consumed, has been consumed or is to be consumed by said infant. In some embodiments, the composition comprising milk is the infant's only source of dietary zinc. In some embodiments, the milk in the composition comprising milk is the infant's only source of dietary zinc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); "Monoclonal Antibodies: Methods and Protocols". Vincent Ossipow, Nicolas Fischer. Humana Press (2014); "Monoclonal Antibodies: Methods and Protocols". Maher Albitar. Springer Science & Business Media (2007), all of which are incorporated by reference. Other general references are provided throughout this document.

Materials and Methods

Chemicals and Reagents

The DNA dye Hoechst 33342 was purchased from Sigma-Aldrich. The cell permeant viable fluorescent zinc probe Zinquin ethyl ester was obtained from Biotium (Hayward, Calif.), whereas Fluozin3-AM was from Thermo Fisher Scientific. Zinc sulfate was obtained from Merck.

Determination of Zinc Concentration in Breast Milk

Fresh human milk samples were collected from mothers and were stored at −20° C. until analyzed. Zinc quantification was performed using electrothermal atomic absorption spectrometry as described previously (Arnaud J., et al., The Analyst, 1992, 117(10):1593). Each sample was quantified in duplicates on two different days.

Genome Sequence Analysis of SLC30A2

The current study was approved by the Institutional Review Board of the RB Rappaport Faculty of Medicine (US-HHS-FWA-00013345, 20-2016). Written consent was obtained from all subjects. Blood samples were derived from two women with low zinc milk concentration and their available family members. DNA was extracted from blood using DNeasy Blood & Tissue Kit (Qiagen). Oligonucleotide primers were designed to amplify each of the 8 exons of ZnT2 as described previously (Lasry I., et al., Journal of Biological Chemistry, 2012, 287(35):29348-61). PCR products were isolated using PCR Clean-up system (Promega Corporation, WI, USA) and sequenced by Hy-labs, Israel.

Sequence Analysis of SLC30A2 mRNA

Fresh human milk was collected from mothers in the morning hours using an electric vacuum pump and the milk was transferred to the laboratory on ice. Milk samples (30 ml) were then centrifuged at 2,000 g for 5 min at 4° C. Total RNA was extracted from the pellet containing the total cell population, using TriReagent (Sigma-Aldrich). cDNA was synthesized from total RNA (1 µg) using a high capacity cDNA reverse transcription kit (Applied Biosystems, Foster city, CA, USA). cDNA was amplified using a 5× ReadyMix PCRmaster mix reaction buffer (ABgene, Surrey, UK; total volume 50 µl) consisting of 10 pmol of each primer according to the instructions of the manufacturer. The primers for the PCR analysis are listed in Table 1. PCR was performed using the following conditions: initial melting at 95° C. for 5 min, followed by 35 cycles each of 1 min at 95° C., annealing of 1 min at 60° C., elongation of 1 min at 72° C., followed by 10 min extension at 72° C. PCR products were isolated using PCR Clean-up system (Promega Corporation, WI, USA) and sequenced by Hy-labs, Israel. Nucleotide numbering is based on the coding sequence (CDS) of SLC30A2 mRNA variant 1 (NM_001004434.2, SEQ ID NO: 1).

TABLE 1 primers used for PCR

| Purpose | Name | Forward | Reverse |
|---|---|---|---|
| Site-directed mutagenesis recapitulating the deletion of 27 bp of ZnT2 | ZnT2-del-839-865 | GGTGTTGATGGAAGC TGTTCGTGATCTGC (SEQ ID NO: 16) | GCAGATCACGAACAG CTTCCATCAACACC (SEQ ID NO: 17) |
| ZnT2 mRNA sequencing | ORF1-ZnT2 | ACTGCATGGAGGCCA AGGAG (SEQ ID NO: 2) | GTCGCCGATCACATG GATG (SEQ ID NO: 3) |
| ZnT2 mRNA sequencing | ORF2-ZnT2 | CTGGTGTACCTGGC TGTGGAG (SEQ ID NO: 4) | TGAGCAGTCAGTCTG AGGGGC (SEQ ID NO: 5) |
| Real-time | A9AA-4mm-ZnT2 | GATCCTGGTGTTGA TGGATGCT (SEQ ID NO: 6) | TGAGCAGTCAGTCTG AGGGGC (SEQ ID NO: 7) |
| Real-time | WT-ZnT2 | CCAAGGGCGTTGAC TTCACA (SEQ ID NO: 8) | GATGTGGACAGACAG AACAGGCTGG (SEQ ID NO: 9) |

Figure 2A:
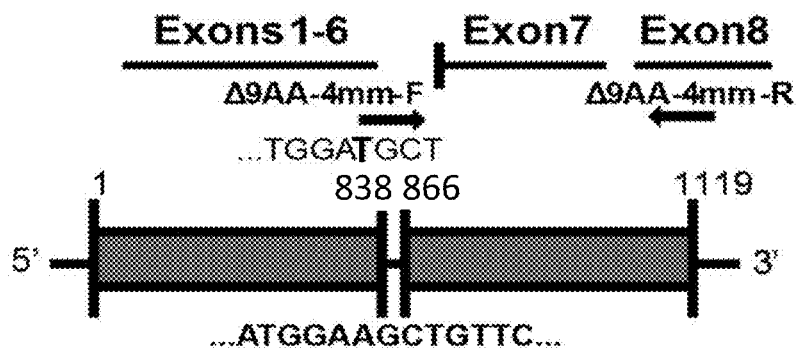
FIGS. 2A-2B. describes allele quantification using real-time PCR analysis. (2A) is a schematic illustration of the difference between WT-ZnT2 and A9AA-ZnT2 mRNA. Arrows represent the location of the real-time PCR primers. Four (4) mm represents the forth nucleotide mismatch 837A>T (gray colored) for better specification of the primer. Nucleotide numbering is based on the coding sequence of SLC30A2/ZnT2 mRNA variant 1 (NM 001004434.2, SEQ ID NO: 1). "F" indicates forward primer. "R" indicates reverse primer. (2B) is a bar chart showing the percent of each ZnT2 allele (WT-ZnT2 or A9AA-ZnT2) expressed relative to total ZnT2 mRNA expression (WT-ZnT2+Δ9AA-ZnT2). Control 1 and Control 2 represent healthy individuals. Asterisks denote that the values were statistically significant when compared to those obtained with control 1 ($p<0.05$). Real-time PCR quantification was performed 3 independent times and mean values are shown. Error bars represent S.D.

Real-Time PCR for Allele Expression Quantification cDNA was synthesized from RNA isolated from the cell fraction derived from breast milk samples obtained from the two mothers and two control healthy individuals with matched infant ages (7 months old). Diagnostic primers were designed to detect the two different alleles i.e. the WT and the truncated Δ9AA variant. The first primer pair was designed to detect only the WT-ZnT2 transcript as the forward primer targeted the 27 bp that were deleted from the mRNA of the Δ9AA variant (FIG. 2A, 844-F). In contrast, the second forward primer was designed to detect only the deleted mRNA and hybridized solely to the mRNA that lacks the 27 bp (FIG. 2A—Δ9AA-4 mm-F). For this purpose, the forward primer contains 19 bp that hybridized with the sequence upstream to the deleted segment, and 2 bp that hybridize following the deletion (FIG. 2A—Δ9AA-4 mm-F). In addition, for better specificity, a mismatch in the fourth nucleotide at the 3' of the forward primer was added 837A>T (FIG. 2A—Δ9AA-4 mm-F). Real-time PCR was performed using an Applied Biosystems-Life Technologies 7300 Real-Time PCR. A quantitative PCR reaction (20 μl) contained 5 ng of cDNA. PerfeCTa SYBR Green FastMix reagent was used (Quantabio, MA, USA). The primers used for allele quantification are listed in Table 1. Real-time PCR was first performed on known template amounts and the threshold cycle (Ct) values obtained with each primer were compared; no difference between the efficacies of the two primers was found. For each sample a triplicate quantification was performed, and the mean Ct calculated. DNA quantification values for each primer pair in each sample were calculated using the parameters of the standard curve (b: intercept; a: slope) as follows: value=$10^{[(Ct-b)/a]}$. For each sample, the percentage of relative expression of each allele from the total expression (total expression was the sum of the two allele values) was calculated.

Expression Vector Construction

ZnT2 bimolecular fluorescence complementation (BiFC) constructs were generated as previously described (Lasry I., et al., Journal of Biological Chemistry, 2012, 287(35): 29348-61). The nucleotide deletion was introduced into the ZnT2 expression plasmids using Pfu Turbo DNA polymerase (QuikChange kit, Stratagene, La Jolla, Calif.) and primers listed in Table 1. The coding region of the Ruby tag was amplified using mRuby-Lifeact-7 expression vector and the primers Xho-pmRuby-F 5'ATACTCGAGACCAT-GAACAGCCTGATCAAA 3' (SEQ ID NO: 11) and mRuby-Xba-R 5' ATATCTAGAT-TACCCTCCGCCCAGGCCG 3' (SEQ ID NO: 12). The PCR products were then sequenced to verify that they contained the correct length of the insert using agarose gel electrophoresis, following which the DNA was purified from the gel using a Promega Wizard SV gel & PCR cleanup system. The purified PCR products were digested with the appropriate restriction enzymes and were cloned into the pcDNA3.1-Zeo-ZnT2-containing vector: a backbone to insert ratio of 1:6 was used. The ligation was performed for 30 min at room temperature and the ligation products were transformed into heat shock competent E. coli DH5α. Positive colonies were selected using PCR. The fidelity of the insert and the tag were confirmed by direct sequencing (Hy-labs, Israel).

BIFC Terminology

YN and YC represent the non-fluorescent N- and C-terminal halves of YFP, respectively. Transfection with the construct-YC-YN implies that plasmids containing the construct-YN and the construct-YC were co-transfected into cells. Construct-YFP indicates that plasmids containing the full-length YFP fluorescent protein were transfected.

Cell Culture, Transient Transfections, Flow Cytometry and Confocal Laser Microscopy MCF-7 breast cancer cells were grown and transiently transfected as previously described (Golan Y., et al., Journal of Biological Chemistry, 2016, 291(26):13546-59) for all the experiments presented here. Twenty-four hours after transfection, cells were stained with Zinquin ethyl ester (40 μM) or Fluozin3-AM (1 μM) and were analyzed using flow cytometry or confocal microscopy, respectively. For the zinc transport function experiments, cells were incubated for 2 hours with growth medium containing 75 μM ZnSO$_4$ before staining. Cells were then rinsed with PBS and incubated in growth medium containing 40 μM Zinquin ethyl ester and were analyzed with a flow cytometer as previously described (Golan Y., et al., Journal of Biological Chemistry, 2016, 291(26):13546-59). For confocal microscopy, cells were incubated in growth medium containing 1 μM Fluozin3-AM for 30 min, following which they were washed 3 times with PBS. Cells were then incubated for another 30 min in growth medium at 37° C. to allow a complete de-esterification of intracellular AM esters. Finally, cells were washed with PBS and then incubated in PBS containing 1 mM MgCl$_2$, 1 mM CaCl$_2$) and 10 mM D-glucose at pH 7.4. Hoechst 33342 (2 μg/ml) was used for viable nuclear DNA staining. Live cells were imaged using an inverted confocal microscope (Zeiss LSM 710) at a magnification of ×63 under immersion oil.

Assessment of ZnT2 Dimerization in BiFC Transfectants Using Western Blot Analysis MCF-7 cells were transiently transfected with the designated plasmids (3 μg in single construct transfection and 1.5 μg DNA of each construct in co-transfections). Membrane proteins were isolated on ice using an extraction buffer as previously described (Golan Y., et al., Journal of Biological Chemistry, 2015, 290(14):9050-63). Briefly, proteins (30 μg) were resolved by electrophoresis on 10% polyacrylamide gels, electroblotted onto cellulose nitrate membranes, blocked with Tris-buffered saline (TBS)-milk and reacted with mouse anti-ZnT2 monoclonal antibody (at 1:2,000 dilution, 1 hr at room temperature; generously provided by Prof. T. Kambe, Kyoto University, Kyoto, Japan). Blots were then washed three times with TBS for 10 min each at room temperature and incubated with horseradish peroxidase-conjugated goat anti-mouse IgG (1:20,000 dilution; Jackson Immunoresearch Labs, West Grove, Pa.) for 1 hr at room temperature. After three washes, enhanced chemiluminescence detection was performed according to the manufacturer's instructions (Biological Industries, Beth-Haemek, Israel). Similarly, actual protein loading onto the SDS-PAGE gels was confirmed by blot reprobing with a rabbit polyclonal antibody against the a subunit of Na$^+$/K$^+$ ATPase (KETTY at 1:3,000 dilution; kindly provided by Prof. S. J. D. Karlish, Weizmann Institute of Science, Rehovot, Israel) and detected with horseradish peroxidase-conjugated goat anti-rabbit IgG (1:15,000 dilution; Jackson Immunoresearch Labs, West Grove, Pa.).

Detection of Native Human ZnT2

Breast milk (30 ml) was centrifuged at 2,000 g for 5 min at 4° C. and was separated into 3 fractions. Membrane protein extraction buffer (100 μl) was added directly to the fraction of cells (bottom fraction). Samples were then incubated on ice for 30 min and centrifuged at 20,000 g for 15 min at 4° C. The fraction containing membrane proteins was collected and proteins (20 μg) resolved by electrophoresis on 10% polyacrylamide gels as described above. Mouse anti-ZnT2 monoclonal antibody was used for Western blot analysis (at 1:3,000 dilution, 1 hr at room temperature). Actual protein loading onto the SDS-PAGE gels was confirmed by blot reprobing with a rabbit polyclonal antibody against actin (at 1:1,000 dilution, overnight at 4° C.; Sigma-Aldrich).

Evaluation of the Half-Life of WT and Mutant ZnT2 Using Cycloheximide Inhibition of Translation MCF-7 cells were seeded and transiently transfected as described above. Sixteen hours after transfection, the growth medium was replaced by fresh medium containing 50 μg/ml cycloheximide (CHX). Membrane proteins were isolated every 0.5-1 hour using an extraction buffer and Western blot analysis was performed as described above.

Quantification of Protein Band Intensity after Western Blot Analysis

Western blot analysis was performed using Quantity One 1-D analysis software, by Bio-Rad Laboratories, Inc.

Statistical Analysis

Results are presented as means±S.D. Statistical comparisons were performed using two tailed Student's t-test (Prism Graph Pad, Berkeley, Calif.), and a significant difference was demonstrated when p value was <0.05. Results from at least three independent experiments are shown.

Database Analysis

Using ExAC exome sequence database of healthy individuals is an objective source for estimation of the frequency of inactivating mutations in the general population and TNZD prevalence, mothers harboring ZnT2 mutations that cause TNZD were not found to have any other related disease and therefore will be included in this database. It is important to recognize that if inactivating ZnT2 mutations will be found to be related to another disease in the future, the prevalence that was estimated herein based on the ExAC database is in fact an underestimation.

Bioinformatics Analysis

Mutation conservation analysis was performed using the Consurf tool, which generated an amino acid conservation map of the ZnT2 CDS. Consurf assigned a conservation range value, from 1-9 to each amino acid position in ZnT2, based on homologous sequence analysis. Amino acid positions with a conservation score range of 1-6 are considered "not conserved", while those with a score of 7 are "somewhat conserved", score 8 are "conserved", and score 9 are "very conserved". One hundred and thirteen ZnT2 missense mutations from the ExAC database were cross-checked with their ConSurf conservation score.

The PROVEAN and Polyphen-2 tools were utilized to predict whether or not the ZnT2 missense mutations found in the ExAC database were functionally deleterious. PROVEAN predicts an impact score, calculated based on sequence variation alignment clustering. A mutation with a score less than the cutoff of −2.5 is considered deleterious to the function of the protein. PolyPhen-2 calculates a score for a mutation's impact on protein function based on homologous sequence clustering algorithm [26]. The algorithm takes into consideration the conservation of the mutated amino acid, as well as amino acid features like surface area, hydrophobicity, amino acid volume, and Ramachandran angles. Polyphen-2 defines "possibly damaging" in a score of 0.45-0.95, and "probably damaging" in a score range of 0.95-1.00, while benign mutations are below a score of 0.453.

The Thermal Stability meta predictor tool was used to predict the effect of ZnT2 missense mutations on protein thermal stability. This tool combines the predictive power of 11 tools to generate two predictive scores, and average from all the tools, and a weighted average which takes into consideration the amino acid environment. The weighted average is considered more accurate. A score of <−0.2 kcal/mol is considered destabilizing. The ZnT2 monomer model was aligned to 3h90 template (PDB 3h90, chains A and C) by the HHpred method. The 3h90 PDB file contains residues 73-277 of ZnT2 only; therefore, only mutations that were within these residues were tested.

Example 1

Clinical Data and Early Genetic Diagnosis of TNZD

Figure 1B:
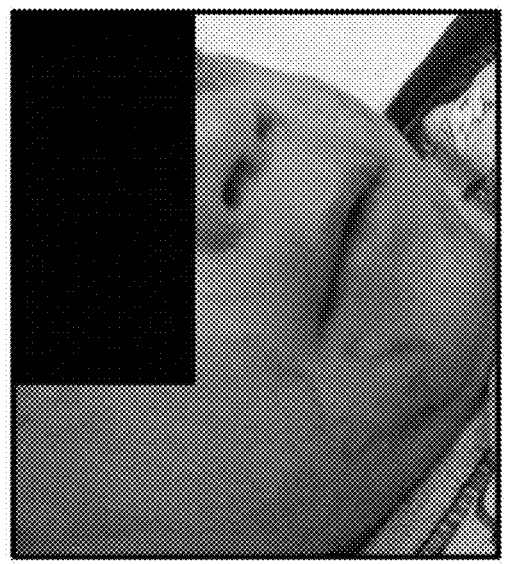

An exclusively breast-fed, preterm infant (Son 1 in FIG. 1A) suffered from a severe erythematous scaly rash involving his face, neck, and diaper area at the age of 13 weeks (FIG. 1B). The rash was first diagnosed as recalcitrant seborrheic dermatitis with possible secondary impetigo. Therefore, the infant was treated with different ointments including topical antibiotics and steroids without improvement. After 3 weeks of worsening skin condition, physicians considered the possibility of zinc deficiency, and the infant's plasma zinc levels were found to be extremely low (4.5 µg/dL; normal range 55-165 µg/dL). Zinc supplementation (5 mg/day) was initiated and within 4-5 days of supplementation, the infant's appetite improved, and weight gain was restored. The skin rash completely vanished within 2 weeks.

Mother 1's sister, Mother 2, (FIG. 1A) had also recently given birth, and had a 4-month-old baby girl (Daughter 2 in FIG. 1A) without any symptoms of zinc deficiency. After genetic screening of breast milk cells from both mothers, a common mutation in ZnT2 mRNA was found (described herein below). As a result, zinc blood levels in Mother 2's exclusively breastfed daughter were measured and indeed the infant displayed a mild zinc deficiency (41 µg/dL, normal range 55-165 µg/dL). It should be noted, that Daughter 1 (a previous child of Mother 1, FIG. 1A) was also exclusively breastfed; however, Mother 1 did not notice any unusual symptoms in her daughter. Likely, the infant had only a mild zinc deficiency like her cousin, which was not associated with apparent symptoms. Such a deficiency would be completely cured after weaning, due to zinc uptake from food. Breast milk zinc concentrations were only 6 and 11 µg/dL for Mother 1 and Mother 2, respectively (normal median range 85 µg/dL at 7 months of lactation, minimum level 44 µg/dL and maximum level 136 µg/dL) (Dorea J G., Nutritional Research, 2000, 20(11): 1645-1687).

Example 2

DNA and RNA Sequencing

Figure 1C:
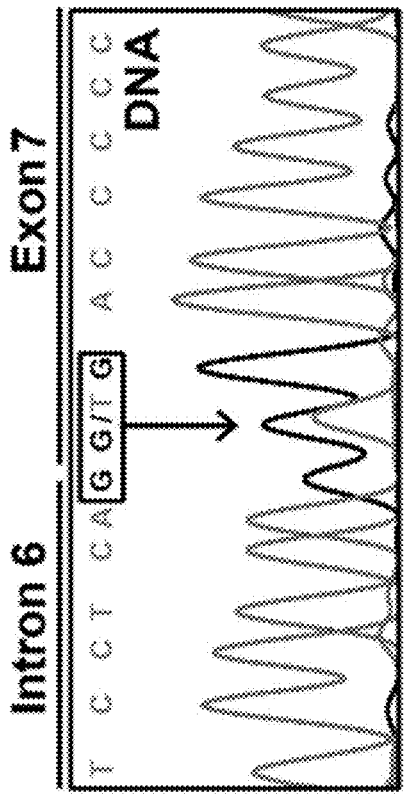
Figure 1D:
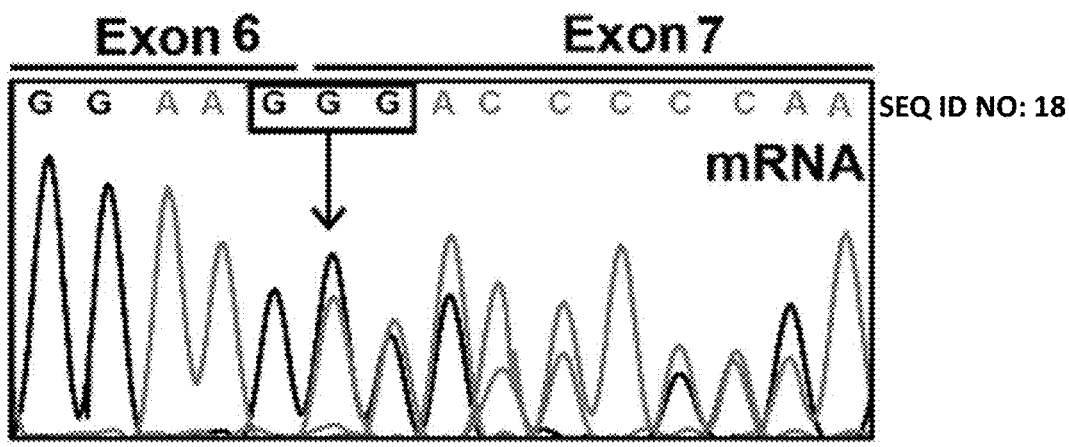

DNA sequencing of Mother 1 and Mother 2 identified a single nucleotide shift resulting in a synonymous mutation of guanine to adenine at position 546 (546G>A) (Nucleotide number 1 refers to the first nucleotide of the ATG codon of the long ZnT2 mRNA variant 1, NM_001004434.2, SEQ ID NO: 1) which does not alter the protein sequence (Ser182). Furthermore, this genomic DNA sequencing identified a single nucleotide missense mutation of guanine to thymine at position 839 (839G>T) (FIG. 1C). This missense mutation was initially predicted to result in a single amino acid substitution of valine in place of glycine (Gly280Val). However, it was recently shown that the guanine at position 838 in ZnT2 is an alternative splice site, and thus a mutation at position 839 might affect splicing. Therefore, further experiments to explore the impact of this genomic 839G>T mutation on the splicing of ZnT2 mRNA were performed. Sequencing of mRNA isolated from breast milk cells revealed that the missense genomic mutation 839G>T did indeed result in alternative 3' splicing, and exon skipping. This alternative splicing deleted the 27 base pairs (bp) from position 839 to 865 (839_865del). As shown in FIG. 1D, starting with nucleotide 839, mRNA sequence analysis revealed two distinct mRNAs: a WT mRNA and a 27 bp-truncated transcript resulting from skipping of a 5'-region of exon 7. The same findings were observed upon DNA and RNA sequencing in Mother 1 and Mother 2.

Figure 1E:
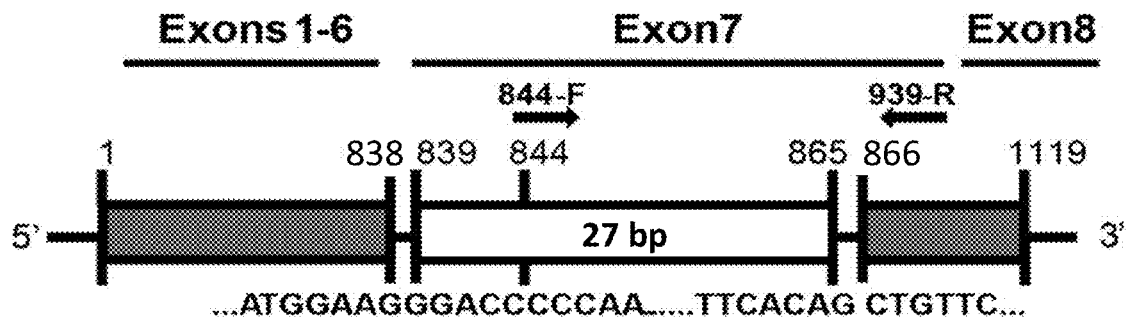

TA cloning of the PCR products was performed, and the insert-harboring plasmids were sequenced in order to verify the exact nucleotide sequence of the truncated ZnT2 allele. The 27 bp skipping resulted in a substitution of glycine to alanine (Gly280Ala) along with a deletion of 9 amino acids encompassing threonine 281 to alanine 289 (Thr281 Ala289del) (FIG. 1E). The 9-amino acid truncation of this exon skipped ZnT2 variant was termed Δ9AA. These results show that both the WT and the Δ9AA variant alleles are expressed and also highlight the importance of performing a gene expression screen at the mRNA level upon identification of a genomic SLC30A2/ZnT2 mutation.

Example 3

Development of Diagnostic Primers

In order to understand the molecular mechanism underlying the presumed haploinsufficieny of TNZD, whether or not the WT and truncated alleles are equally distributed was assessed. In order to quantify the distribution of the WT and the truncated ZnT2 mRNA alleles, diagnostic primers were designed. The first set of primers was designed to detect solely the WT-ZnT2 allele, with the forward primer within the 27 base pairs unique to the WT mRNA (FIG. 2A). In contrast, the second forward primer was selected to detect only the truncated ZnT2 mRNA (Δ9AA) by hybridizing to the unique junction of exon 6 and truncated exon 7 of the mRNA lacking the 27 bp (FIG. 2A and Materials and Methods).

Figure 2B:
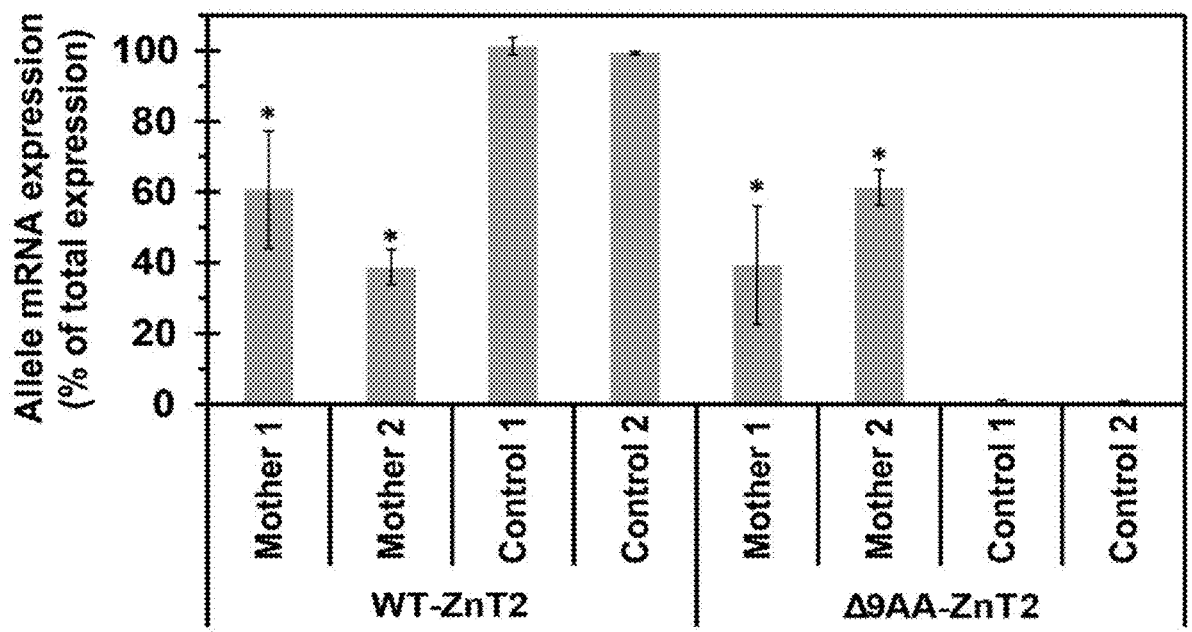

Two healthy control individuals (Control 1,2 FIG. 2B) expressed only the WT-ZnT2 allele, while the two mothers harboring TNZD-associated mutations, expressed between 40-60% of the WT allele with the remaining transcript being the truncated Δ9AA allele (Mother 1,2 FIG. 2B). These results demonstrate that the two alleles were comparably expressed in both Mother 1 and Mother 2. These findings also show, for the first time, that a haploinsufficieny state exists for the WT allele in TNZD pathogenesis.

Example 4

A Native Human ZnT2 Variant (40 kDa) is Expressed in Breast Milk Cells

Figure 3:
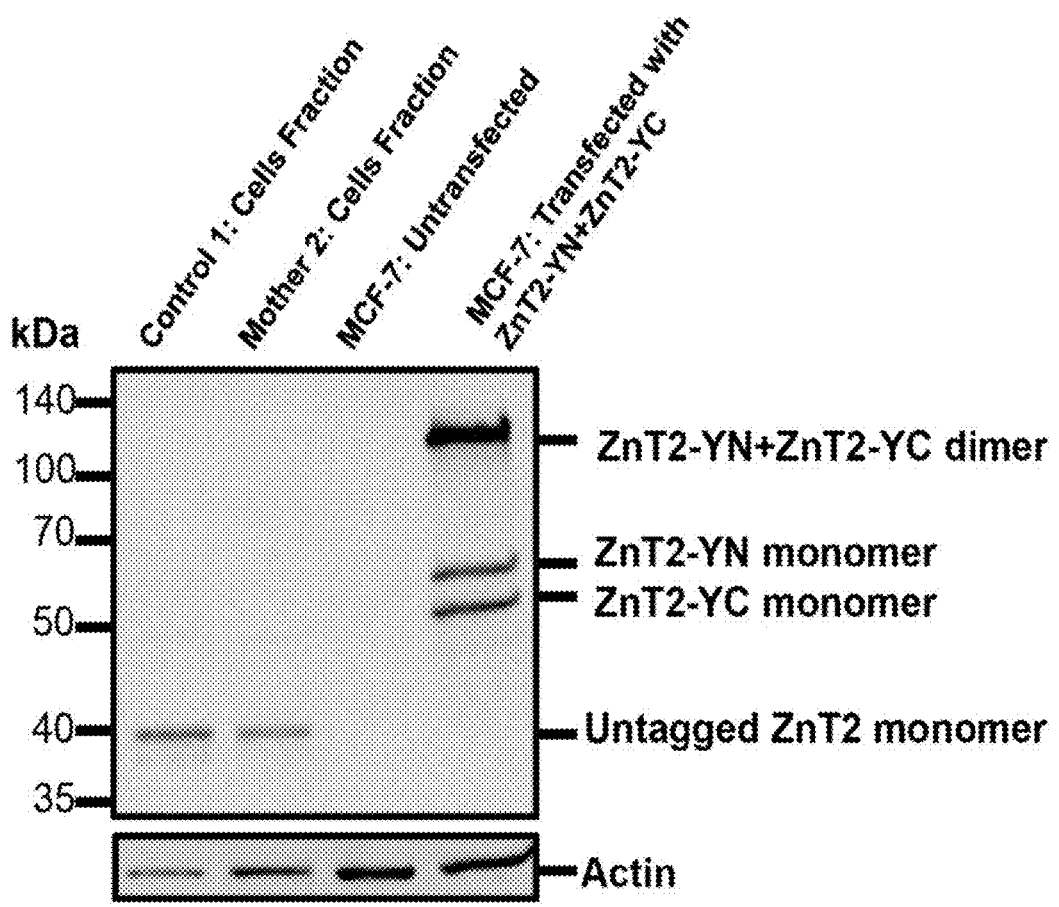
FIG. 3 is an image of a western blot analysis performed under denaturing SDS-PAGE conditions using membrane proteins extracted from the cellular fraction of breast milk or MCF-7 cells. The native expression of human ZnT2 in a mother of a TNZD patient is shown; antibodies used were against ZnT2 and β-actin.

In order to verify the expression of the WT native ZnT2 protein in women with zinc-deficient breast milk, membrane proteins were extracted from the breast milk cell fraction. Both mutant and control cells expressed predominantly the 40 kDa variant of WT ZnT2, which corresponds to SLC30A2 mRNA variant 1 referenced previously (FIG. 3). The 9-amino acid deletion in the ZnT2 protein could not be uniquely detected on SDS-PAGE, and therefore it could not be determined whether the Δ9AA variant protein was expressed. However, these findings lend further support to the suggestion that a haploinsufficiency state occurs for the unaffected WT allele, resulting in production of zinc-deficient breast milk. Although mother 2 had ~50% of the WT levels of the ZnT2 protein, her breast milk was zinc-deficient and lead to a mild zinc deficiency in her infant.

Example 5

Figure 4A:
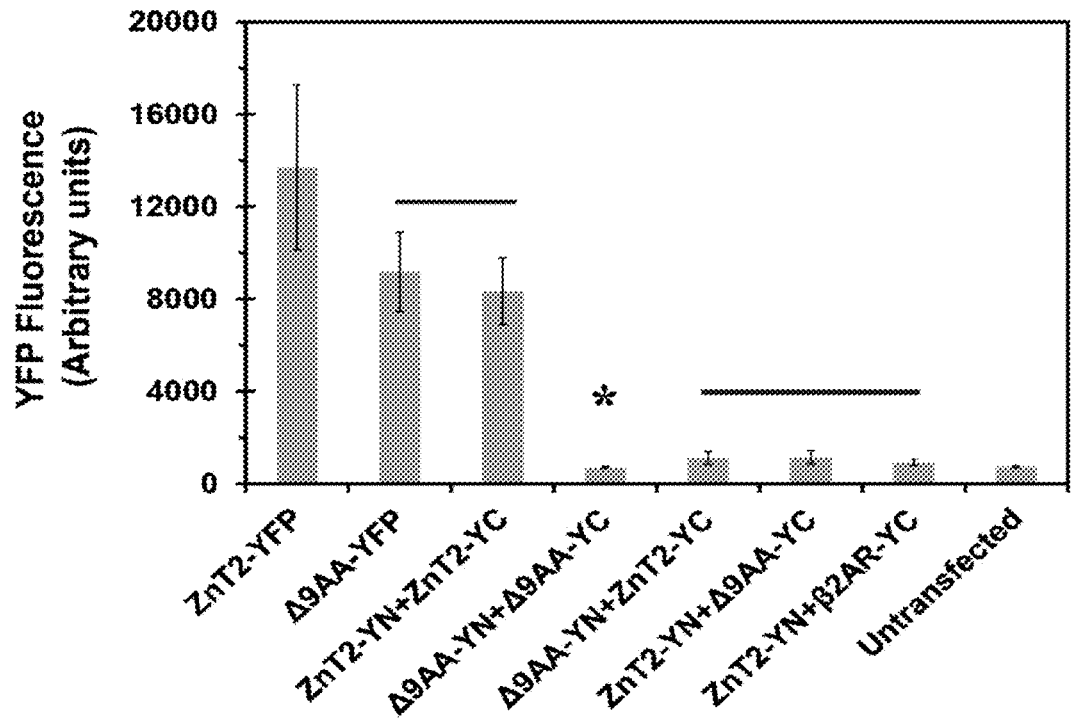
FIGS. 4A-4C demonstrate a Δ9AA-ZnT2 protein does not form homodimers. (4A) is a bar chart depicting flow cytometry-based, histogram quantification of YFP fluorescence (Y axis). The constructs that were used for transfection are listed in the X axis. Values that are not statistically significant from one another ($p>0.05$) are connected by a line; in addition, asterisks indicate that the value below was not statistically different from the value obtained with untransfected cells. Error bars represent S.D. (4B) are representative confocal micrographs. YFP fluorescence is artificially presented (green fluorescence). Red fluorescence represents co-transfection with the RFP vector as a positive control for transfection. Hoechst 33342 (blue fluorescence) was used to stain nuclei. A magnification of ×63 under immersion oil was used. (4C) is an image of a western blot analysis of monomers and homodimers of the various WT- and Δ9AA ZnT2 constructs using an anti-ZnT2 antibody (Upper panel). α-subunit of $Na^+/K^+$ ATPase was used to confirm equal protein loading (lower panel).

The Alternative 3' Splice Variant (Δ9AA) Associated with TNZD does not Homodimerize The ability of the alternative 3' splice variant (Δ9AA) ZnT2 to form homodimers was evaluated using the bimolecular fluorescence complementation (BiFC) assay that has been previously applied for the detection of in situ dimerization of ZnT2 and other ZnTs in living cells. High YFP fluorescence intensity indicates a strong interaction between the two tagged proteins, as this enables the refolding of the two non-fluorescent halves of YFP (YN and YC) into a fully fluorescent protein. As determined by flow cytometry, it was found that the alternative 3' splice ZnT2 variant which lacks 9 amino acids in the C-terminus, lost the ability to form homodimers (FIG. 4A, Δ9AA-YN+Δ9AA-YC). It was further found that Δ9AA-ZnT2 failed to form homodimers with native WT-ZnT2 (FIG. 4A, ZnT2-YN+Δ9AA-YC and Δ9AA-YN+ZnT2-YC). The YFP fluorescence that was observed in all transfections with the truncated Δ9AA-ZnT2 construct was at the background level observed after the negative control WT-ZnT2-YN+β2AR-YC co-transfection. Notably, upon transfection of the Δ9AA-YFP construct relatively high levels of YFP fluorescence was observed, which confirms expression of the Δ9AA-ZnT2 protein. However, the YFP fluorescence levels of the Δ9AA-YFP protein were lower than WT-ZnT2-YFP levels, indicating that the deletion of this 9-amino acid segment at the C-terminus possibly decreases the expression and/or stability of this truncated ZnT2 protein.

Figure 4B:
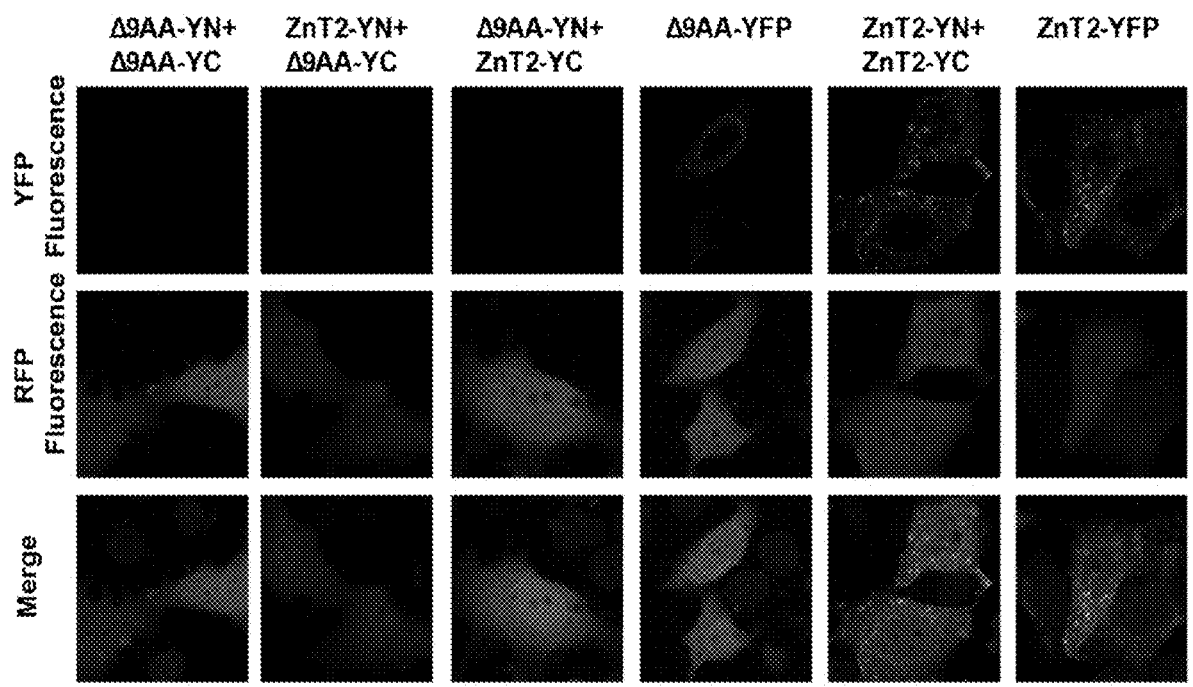

These results were confirmed using confocal laser microscopy (FIG. 4B). YFP fluorescence was neither detected upon co-transfection of the Δ9AA-YN+Δ9AA-YC constructs nor upon co-transfection of the Δ9AA-YC+ZnT2-YN, or the Δ9AA-YN+ZnT2-YC constructs (FIG. 4B). Δ9AA-YFP protein was visible, though again at lower levels that the WT-ZnT2-YFP. These findings indicate that the truncated Δ9AA-ZnT2 protein has lost its homodimerization capacity, and further show that the truncated Δ9AA-ZnT2 protein cannot exert a dominant negative effect over the WT-ZnT2 protein, as it cannot form dimers.

Figure 4C:
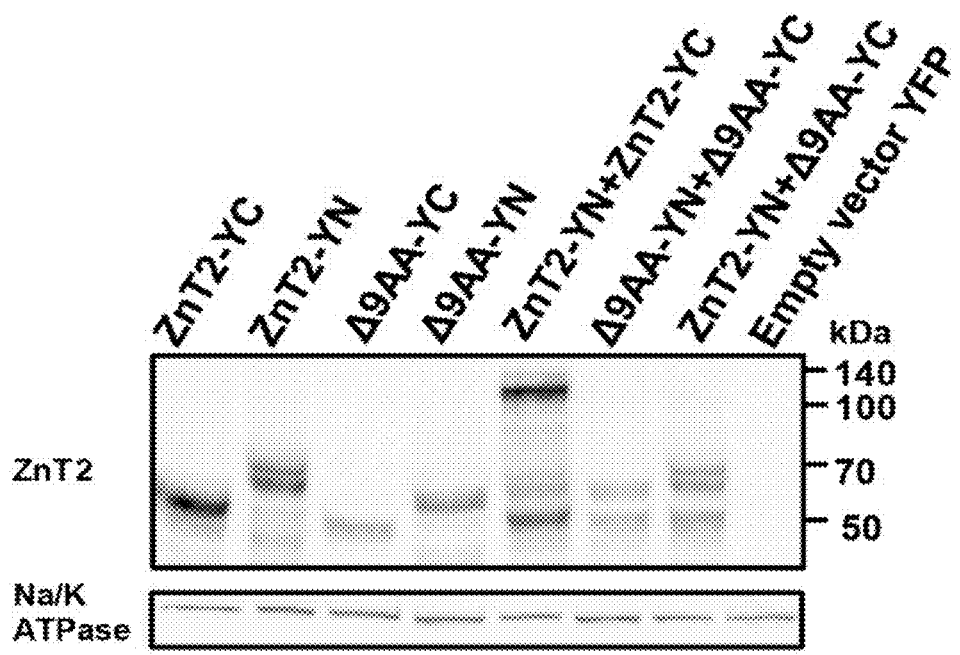

The dimerization results were further confirmed by western blot analysis. Upon dimerization of WT ZnT2-YN with ZnT2-YC, the BiFC tags refold and tightly interact as a result of the formation of multiple hydrogen bonds, thereby forming dimers that are metastable in SDS-PAGE (FIG. 4C). Upon transfection of either Δ9AA-YN or Δ9AA-YC constructs, lower ZnT2 levels are once again observed as compared to transfection of WT-ZnT2 (FIG. 4C). However, in contrast to the ZnT2 protein which was predominantly present in the homodimer form (FIG. 4C, uppermost band), upon co-transfection of Δ9AA-YN+Δ9AA-YC no homodimers were detected (FIG. 4C). Furthermore, upon co-transfection of ZnT2-YN and Δ9AA-YC, the protein levels of both were substantial, yet no homodimers were detectable (FIG. 4C, right side). These results indicate that the lower expression levels or increased degradation of the truncated Δ9AA ZnT2 protein are not the causes for the loss of dimerization capacity. Rather, these findings suggest that the deleted C-terminal region of ZnT2 has a major role in protein-protein interactions and dimer formation.

Example 6

Δ9AA-ZnT2 Protein Undergoes Enhanced Degradation

Figure 5A:
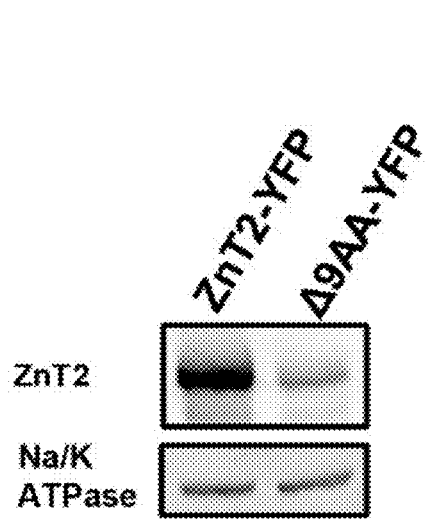
FIGS. 5A-5D demonstrate the truncated Δ9AA-ZnT2 protein undergoes rapid degradation. (5A) is an image of a western blot analysis showing protein levels in transiently transfected MCF-7 cells using an anti-ZnT2 antibody (upper panel), or anti α-subunit of $Na^+/K^+$ ATPase to confirm equal protein loading (lower panel). (5B) is a bar graph summarizing the quantification of the average protein levels from 3 independent experiments as shown in 5A. (5C) is an image of a western blot analysis after cycloheximide (CHX) treatment. (5D) is a graph showing quantification of the western blot bands shown in FIG. 5C, specifically showing the half-life ($t_{1/2}$) of WT-ZnT2-YFP and Δ9AA-ZnT2-YFP proteins. Asterisks represent statistically significant differences ($p<0.05$) relative to WT-ZnT2-YFP, at the same time point. Error bars represent S.D.
Figure 5B:
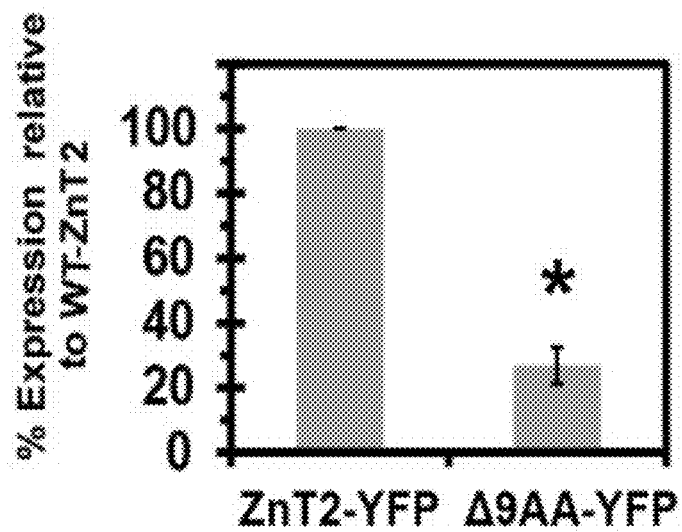

As the above flow cytometry, microscopy and western blot results suggest enhanced degradation of the Δ9AA-ZnT2 protein, direct quantification of protein levels was performed after transient transfection (FIG. 5A). It was found that 24 hours after transfection, the Δ9AA-ZnT2 protein was expressed at a level that was ~25% that of the WT protein (FIG. 5B).

Figure 5C:
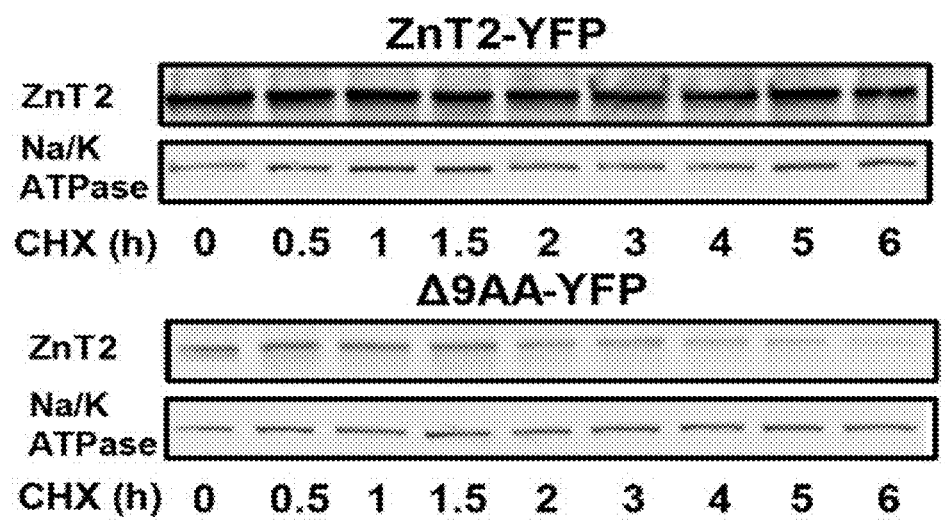
Figure 5D:
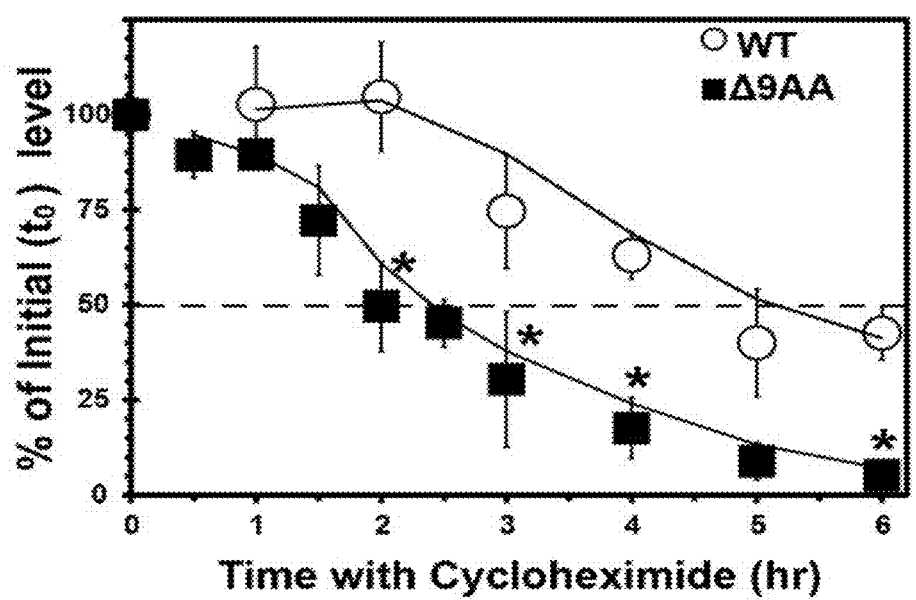

In order to determine the molecular basis underlying the decreased Δ9AA-ZnT2 protein levels, the half-lives of the truncated Δ9AA-ZnT2 and the WT ZnT2 proteins were directly determined using the cycloheximide (CHX) treatment method (see Materials and Methods). It was found that the levels of the truncated Δ9AA-ZnT2 protein were already significantly lower at time $t_0$ compared to the WT ZnT2 protein, but more importantly, the degradation rate of the Δ9AA-ZnT2 protein was visibly enhanced when compared to that of the WT ZnT2 protein (FIG. 5C). Quantification of the ZnT2 bands from western blot analysis revealed that the half-life ($t_{1/2}$) of the WT-ZnT2-YFP protein was ~4.5 hours, whereas that of the truncated Δ9AA-ZnT2-YFP protein was only ~2 hours (FIG. 5D). These results provide direct evidence of the enhanced degradation of the Δ9AA-ZnT2 protein, hence providing a molecular basis for the low expression levels observed with the truncated Δ9AA-ZnT2 protein.

Example 7

Figure 6A:
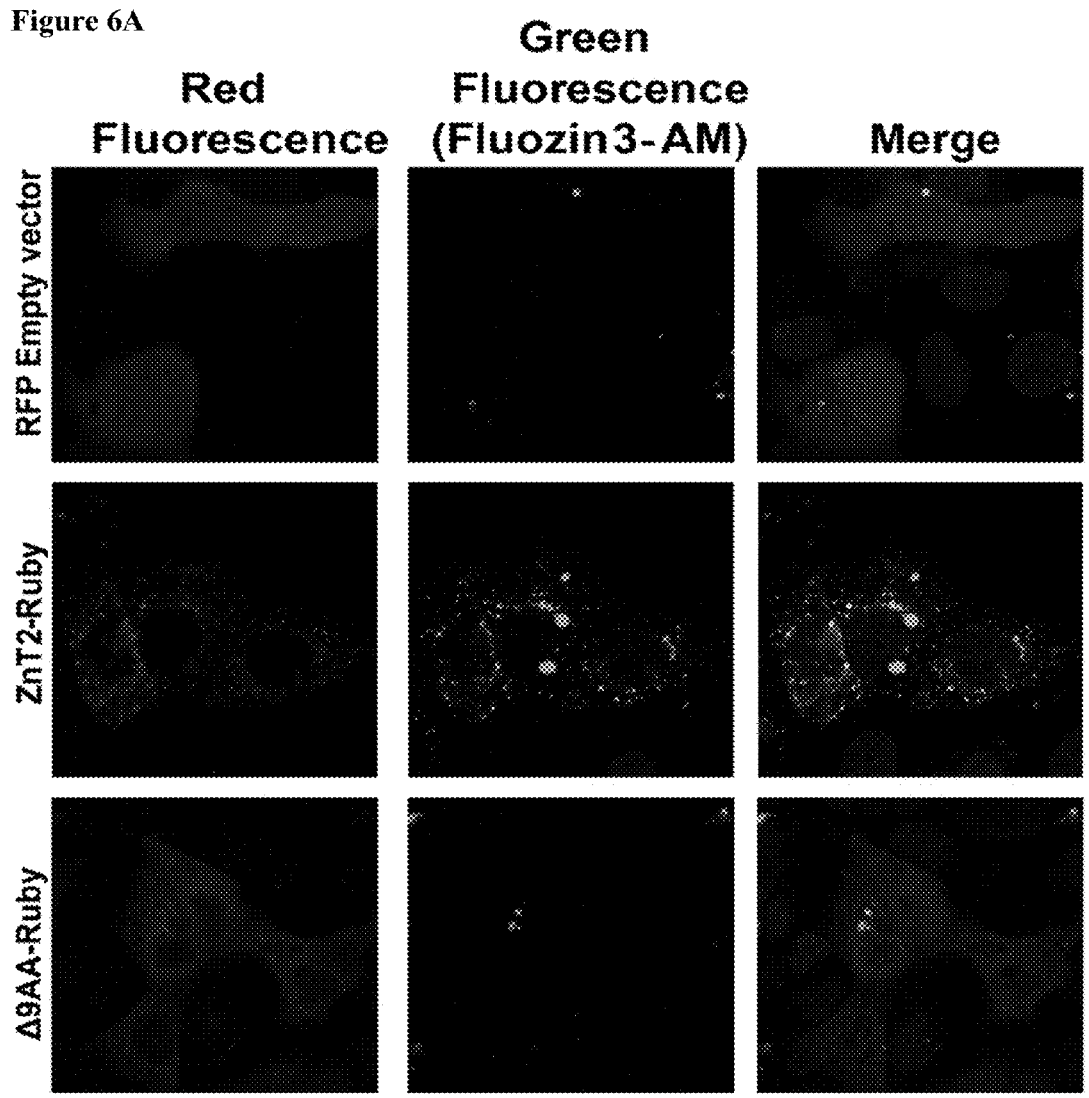
FIGS. 6A-6B demonstrate the Δ9AA-ZnT2 variant is not active in zinc transport into intracellular vesicles. (6A) are micrographs of transfected MCF-7 cells. Fluozin3-AM (green fluorescence) indicates zinc accumulation. Red fluorescence shows the WT-ZnT2-Ruby, the Δ9AA-Ruby, or the RFP-empty vector constructs. Hoechst 33342 (blue fluorescence) was used to stain nuclei. A magnification of ×63 under immersion oil was used. (6B) is a bar graph depicting Zinquin fluorescence levels in MCF-7 cells transfected with the constructs depicted along the X-axis. Zinquin fluorescence was determined using flow cytometry only for cells displaying YFP fluorescence (positively transfected cells) and not for the entire cell population. Asterisks indicate that the values obtained are significantly different ($p<0.05$) when compared with the YFP Empty vector. Error bars represent S.D.

The Alternative 3' Splice Variant Δ9AA ZnT2 is Devoid of Zinc Transport Function In order to determine whether or not the truncated Δ9AA ZnT2 protein retained zinc transport activity, two distinct viable fluorescent zinc probes, Fluozin-3 AM and Zinquin ethyl-ester were used. MCF-7 cells transfected with the tagged WT-ZnT2-Ruby exhibited a high number of fluorescent intracellular vesicles upon staining with Fluozin-3, a cell-permanent fluorescent zinc indicator (FIG. 6A, middle row). This confirmed the key role that the WT ZnT2 plays in compartmentalization of zinc in intracellular vesicles. In contrast, upon transfection with the truncated Δ9AA-Ruby, low levels of red fluorescence were observed, consistent with the fast degradation of the Δ9AA-Ruby protein. Additionally, a very low number of intracellular zinc-containing vesicles were observed (FIG. 6A, bottom row); this background number of Fluozin-3-stained vesicles in the Δ9AA-Ruby transfected cells was similar to that observed upon transfection with the RFP-Empty vector (FIG. 6A, top row).

Figure 6B:
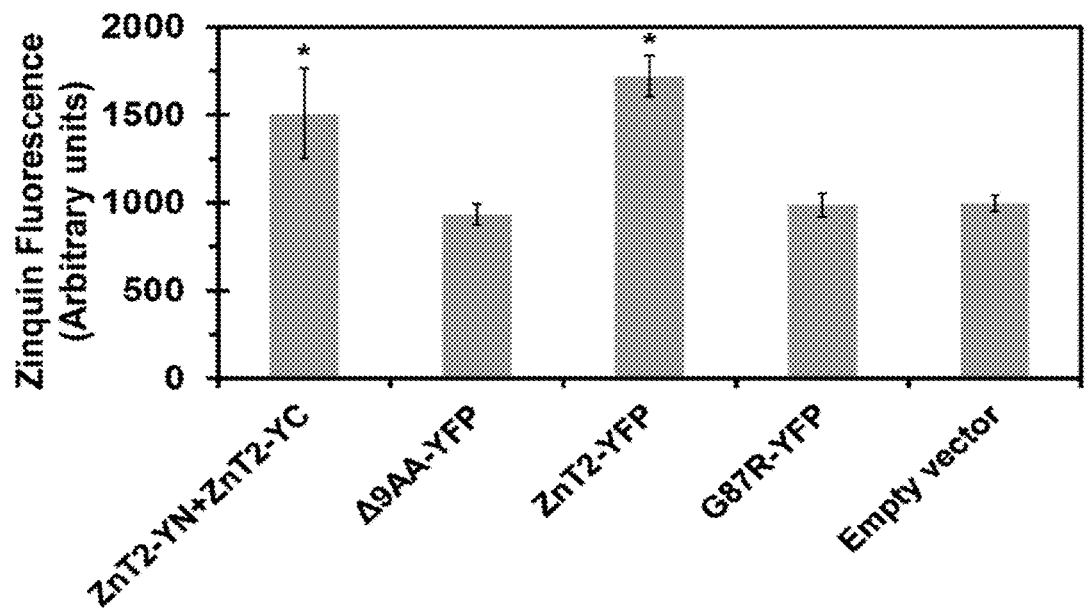

The second fluorescent zinc probe that was used was Zinquin ethyl-ester which has previously been employed to follow zinc accumulation in intracellular vesicles. In contrast to the zinc transport activity of WT-ZnT2-YFP and WT-ZnT2-YC-YN, the truncated Δ9AA-YFP protein failed to mediate the accumulation of zinc in intracellular vesicles (FIG. 6B). The low levels of Zinquin fluorescence observed were similar to the background levels observed upon transfection of YFP empty vector, as well as the levels seen with transfection of the dominant negative Gly87Arg ZnT2 mutant. This mutant was previously showed to be devoid of zinc transport activity. These results indicate that the Δ9AA-ZnT2 variant does not have the ability to transport zinc into intracellular vesicles.

Example 8

Figure 7A:
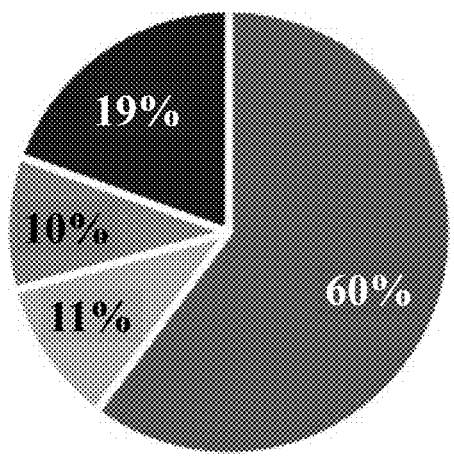
FIGS. 7A-7D demonstrate predictions of missense ZnT2 mutation conservation and effect on protein function. (7A) is a pie chart of the conservation rates of 113 missense mutations that were found in ZnT2 in the ExAC database and were analyzed using ConSurf software. (7B) is a pie chart of PROVEAN prediction of 113 ZnT2 missense mutations which appear to have a deleterious effect. (7C) is a pie chart of PolyPhen-2 prediction of 113 ZnT2 missense mutations which appear to have a deleterious effect. (7D) is a Venn diagram showing the percentage of mutations in conserved residues (based on Consurf analysis) that were predicted to have a deleterious effect of ZnT2 function using PROVEAN and PolyPhen-2 analysis.
Figure 7B:
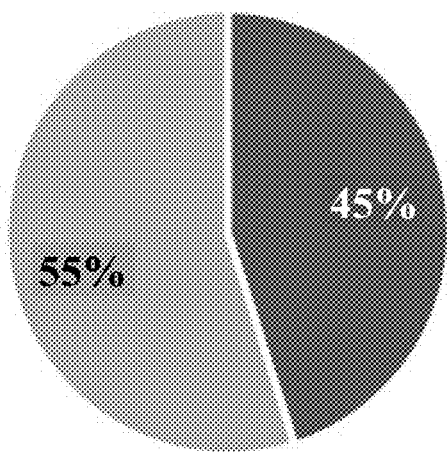
Figure 7C:
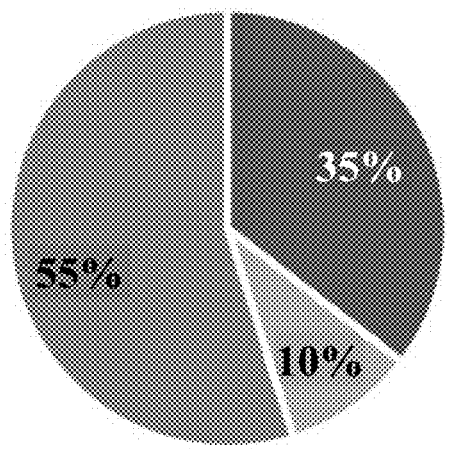
Figure 7D:
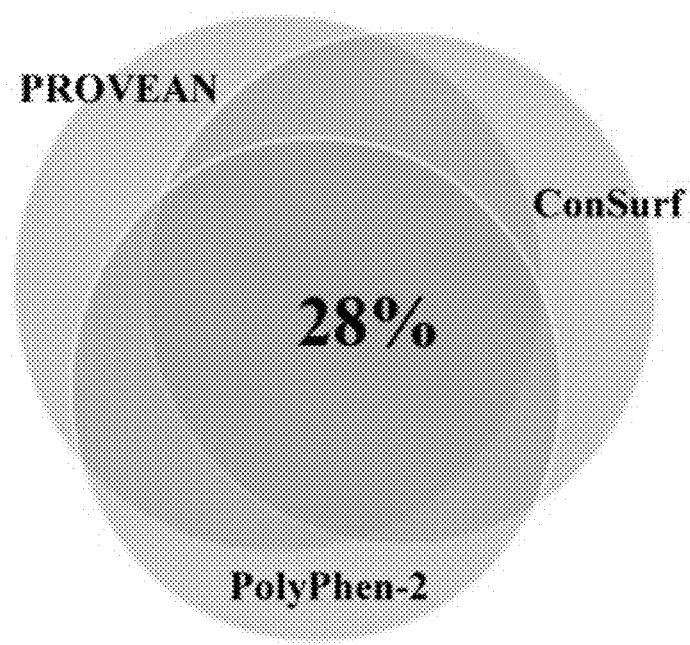

Bioinformatics Analysis of ZnT2 Missense Mutations Predicts at Least 32 Mutations have a Deleterious Impact on ZnT2 Stability and Transport Function The primary aim of the current study was to determine the frequency of missense ZnT2 mutations that are causative of TNZD. According to the ExAC database, in a population of 60,000 healthy humans, obvious definitive LoF mutations (including gain of premature stop codon, splice donor, and frameshift) in ZnT2 occur at a frequency of 1/30,000. In sharp contrast, missense ZnT2 mutations occur at a much higher frequency of 1/117. ZnT2 mutations in conserved residues are more likely to be deleterious. According to Consurf, 40% of the missense mutations listed in the ExAC database occur in conserved regions, with 19% of all mutations mapping to very conserved residues (FIG. 7A). To further analyze ZnT2 missense mutations, the inventors undertook a bioinformatics prediction to determine whether or not the mutations were deleterious. Using PROVEAN analysis and PolyPhen-2 data the inventors found that 45% of the 113 ZnT2 missense mutations were predicted to be deleterious (FIGS. 7B-C). To narrow down the list of ZnT2 missense mutations considered to be deleterious, the inventors cross-analyzed the prediction data of ConSurf, PROVEAN, and PolyPhen-2 for the 113 ZnT2 missense mutations. Thirty-two (32) missense mutations in ZnT2 i.e. 28% out of 113 mutations studied were predicted to be deleterious by both PROVEAN and PolyPhen-2, as well as conserved by Consurf. PROVEAN and PolyPhen-2 analyses only predict 45 mutants, or 39% of the 113 to be deleterious. A list of 45 mutations which were predicted to have a deleterious effect on ZnT2 function based on PROVEAN and PolyPhen-2 analysis are presented (Table 2). In order to select ZnT2 missense mutations to be functionally tested for actual zinc transport capability, thermal stability meta-predictions, structural analysis, and literature comparison were performed. Thermal stability meta-prediction calculations, were performed on the mutations which are listed in Table 2. The localization of each residue was noted using Chimera.

TABLE 2

Degree of conservation and thermal stability of 45 mutations that were predicted to be deleterious for ZnT2 function based on PROVEAN and PolyPhen2 analyses

| | Deleterious ZnT2 mutations predicted by Provean and PolyPhen-2 | ConSurf | Simple average (K cal/mol) | Meta prediction (K cal/mol) |
|---|---|---|---|---|
| 1 | Y19S | | | |
| 2 | H54Y | very conserved | | |
| 3 | R72C | | | |
| 4 | R72H | | | |
| 5 | M85I | very conserved | −0.17 | 0.95 |
| 6 | G87R | | −0.14 | −0.04 |
| 7 | T102A | conserved | −0.68 | −0.2 |
| 8 | A104S | very conserved | −0.32 | −0.07 |
| 9 | A104T | very conserved | 0.47 | 0.65 |
| 10 | H106Y | very conserved | 0.22 | 0.82 |
| 11 | S113T | conserved | 0 | 0.91 |
| 12 | W122C | | −2.89 | −3.18 |
| 13 | R126Q | somewhat conserved | | |
| 14 | A144S | very conserved | −1.06 | −1.18 |
| 15 | V154M | conserved | −0.04 | 0.52 |
| 16 | G156V | very conserved | 0.66 | 0.65 |
| 17 | R165W | very conserved | 0.91 | 1.69 |
| 18 | R165Q | very conserved | −0.25 | 0.39 |
| 19 | G175R | | 1.78 | 1.7 |
| 20 | G175W | | 0.96 | 0.85 |
| 21 | T181M | very conserved | | |
| 22 | A185T | conserved | | |
| 23 | N189K | very conserved | −2.45 | −1.94 |
| 24 | I190T | | −2.45 | −1.94 |
| 25 | H197R | conserved | 0.11 | 0.88 |
| 26 | H205D | very conserved | 0.29 | 0.22 |
| 27 | N214K | very conserved | −0.17 | 0.4 |
| 28 | R218Q | very conserved | −0.7 | −0.31 |
| 29 | G226S | very conserved | 0.23 | 0.98 |
| 30 | S231T | very conserved | −1.14 | −0.39 |
| 31 | G233R | very conserved | −0.2 | 0.61 |
| 32 | G223D | very conserved | −0.28 | −0.06 |
| 33 | P245R | conserved | −1.31 | −1.46 |

TABLE 2-continued

Degree of conservation and thermal stability of 45 mutations that were predicted to be deleterious for ZnT2 function based on PROVEAN and PolyPhen2 analyses

| | Deleterious ZnT2 mutations predicted by Provean and PolyPhen-2 | ConSurf | Simple average (K cal/mol) | Meta prediction (K cal/mol) |
|---|---|---|---|---|
| 34 | E246K | | −0.43 | 0.41 |
| 35 | S259A | very conserved | 1.18 | 1.83 |
| 36 | I269T | conserved | −1.05 | −1.35 |
| 37 | E279K | very conserved | | |
| 38 | R291H | | | |
| 39 | G299R | | | |
| 40 | G299W | somewhat conserved | | |
| 41 | V300L | very conserved | | |
| 42 | A310V | somewhat conserved | | |
| 43 | A323T | somewhat conserved | | |
| 44 | V333M | somewhat conserved | | |
| 45 | E355K | very conserved | | |

Example 9

Ten ZnT2 Missense Mutations were Found to have a Deleterious Effect on Zinc Transport Capacity of ZnT2

Figure 8:
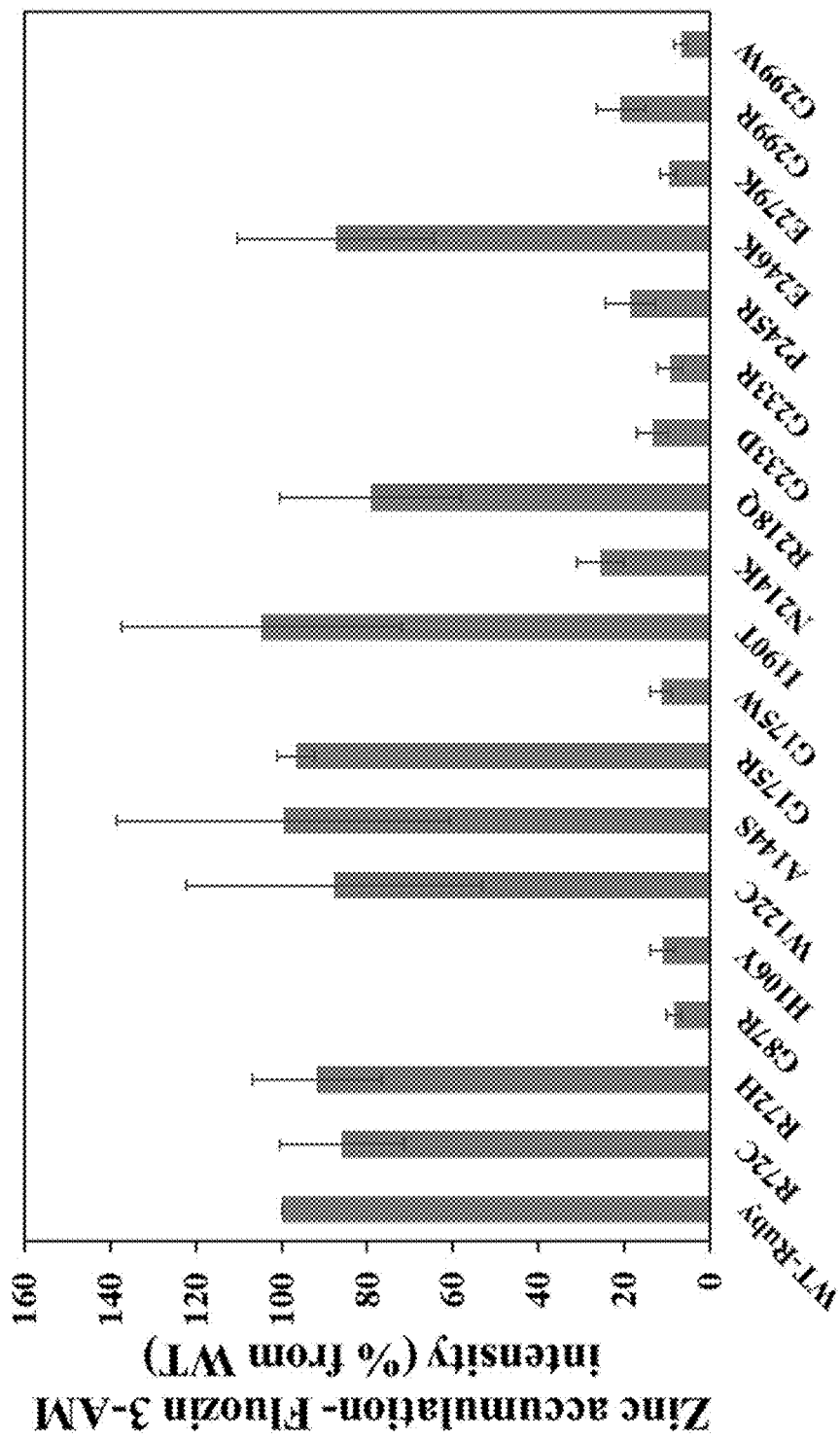
FIG. 8 is a vertical bar graph demonstrating Zinc accumulation function of the different ZnT2 mutants which were found in the ExAC database and were predicted to be deleterious. MCF-7 cells co-transfected with the ZnT2-Ruby constructs containing the mutations depicted along the X axis, were examined for Fluozin3-AM fluorescence levels which reflects actual zinc accumulation. Fluozin3-AM fluorescence was determined using flow cytometry only for cells displaying Ruby fluorescence (transfected cells) and not for the entire cell population. Error bars represent S.D.

The inventors explored the ability of different ZnT2 mutants to accumulate zinc in intracellular vesicles as indicated by the fluorescence intensity of the specific zinc fluorophore Fluozin3-AM in human cells transfected with expression vectors harboring these ZnT2 mutations. Ten (10) out of 18 mutations that were tested failed to accumulate zinc and displayed only residual zinc accumulation of 10-20% compared to the WT-ZnT2 protein (FIG. 8). These LoF missense mutations are predicted to cause TNZD in infants born to mothers carrying these mutations in at least one ZnT2 allele.

Example 10

Prevalence of LoF ZnT2 Mutations Leading to TNZD in the General Population is 1/3,635

In order to determine the prevalence of LoF mutations in ZnT2 in the general population of healthy individuals, the inventors used the allele frequency data of each one of the mutants that were shown to be inactive in zinc transport and were identified in the ExAC database. In addition, one frameshift mutation, one premature stop codon mutation and one mutation in a splice donor site were added to this analysis and considered as bona fide LoF mutation. The p.Glu355Lys (i.e., E355K) mutant was also considered as an inactivating mutation as it was previously shown that a genomic heterozygous mutation which caused this amino acid substitution to lead to TNZD in breast-fed infant. The inventors found that out of 119,969 alleles that were sequenced, 33 were found to carry LoF mutations in ZnT2. Using these data, it was further estimated that the prevalence of a given individual in the general population harboring inactivating heterozygous mutations in ZnT2 is 1/3,635.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A method for reducing the risk of zinc deficiency in a breastfed infant, comprising:
   a. providing a composition comprising breast milk,
   b. determining the presence of a mutation of guanine 839 to thymine in a SLC30A2 polynucleotide derived from said composition comprising breast milk, wherein determining that said mutation is present in said SLC30A2 polynucleotide indicates that said composition has a low zinc content, and
   c. administering zinc to a breastfed infant consuming said composition determined as having low zinc content, thereby reducing the risk of zinc deficiency in the breastfed infant.

2. The method of claim 1, further comprising diagnosing transient neonatal zinc deficiency (TNZD) in said infant, wherein determination of the presence of said mutation determines said infant is afflicted with TNZD.

3. The method of claim 1, wherein a wildtype SLC30A2 polynucleotide comprises a polynucleotide sequence as set forth in SEQ ID NO: 1.

4. The method of claim 1, wherein said SLC30A2 polynucleotide is a DNA molecule, a mRNA molecule or a cDNA molecule made from said mRNA molecule.

5. The method of claim 1, wherein said mutation reduces stability of said mRNA, reduces translation of said mRNA, reduces the level of ZnT2 protein produced, reduces homodimerization of ZnT2 protein produced, reduces zinc binding by ZnT2 protein produced, reduces zinc transport by ZnT2 protein produced, or a combination thereof.

6. The method of claim 1, wherein said determining comprises sequencing of said polynucleotide.

7. The method of claim 6, wherein said sequencing employs at least one oligonucleotide with at least 70% homology to at least one sequence selected from the group consisting of: ACTGCATGGAGGCCAAGGAG (SEQ ID NO: 2)
CTGGTGTACCTGGCTGTGGAG, (SEQ ID NO: 4), and TGAGCAGTCAGTCTGAGGGGC (SEQ ID NO: 5).

8. The method of claim 7, wherein said sequencing employs at least one oligonucleotide comprising at least one sequence selected from the group consisting of:
ACTGCATGGAGGCCAAGGAG (SEQ ID NO: 2)
CTGGTGTACCTGGCTGTGGAG, (SEQ ID NO: 4), and TGAGCAGTCAGTCTGAGGGGC (SEQ ID NO: 5).

9. The method of claim 1, wherein said determining comprises PCR analysis of a DNA or a cDNA polynucleotide.

10. The method of claim 9, wherein said PCR analysis employs at least one oligonucleotide with at least 70% homology to at least one sequence selected from the group consisting of: GATCCTGGTGTTGATGGATGCT (SEQ ID NO: 6), TGAGCAGTCAGTCTGAGGGGC (SEQ ID NO: 7), and GATGTGGACAGACAGAACAGGCTGG (SEQ ID NO: 9).

11. The method of claim 10, wherein said PCR analysis employs at least one oligonucleotide comprising at least one sequence selected from the group consisting of: GATCCTGGTGTTGATGGATGCT (SEQ ID NO: 6), TGAGCAGTCAGTCTGAGGGGC (SEQ ID NO: 7), and GATGTGGACAGACAGAACAGGCTGG (SEQ ID NO: 9).

12. The method of claim 10, wherein said PCR analysis employs at least one oligonucleotide with at least 70% homology to said sequence GATCCTGGTGTTGATGGATGCT (SEQ ID NO: 6).

* * * * *